United States Patent
Feiweier et al.

(10) Patent No.: US 11,921,180 B2
(45) Date of Patent: Mar. 5, 2024

(54) METHOD AND SYSTEM FOR CONTROLLING A MAGNETIC RESONANCE IMAGING SYSTEM

(71) Applicant: Siemens Healthcare GmbH, Erlangen (DE)

(72) Inventors: Thorsten Feiweier, Bavaria (DE); Bryan Clifford, Malden, MA (US); Tom Hilbert, Lausanne (CH)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/553,433

(22) Filed: Dec. 16, 2021

(65) Prior Publication Data

US 2022/0187401 A1    Jun. 16, 2022

(30) Foreign Application Priority Data

Dec. 16, 2020  (EP) .................................... 20214502

(51) Int. Cl.
| | |
|---|---|
| *G01R 33/54* | (2006.01) |
| *G01R 33/44* | (2006.01) |
| *G01R 33/483* | (2006.01) |
| *G01R 33/565* | (2006.01) |
| *G01R 33/56* | (2006.01) |

(52) U.S. Cl.
CPC ......... *G01R 33/543* (2013.01); *G01R 33/446* (2013.01); *G01R 33/4835* (2013.01); *G01R 33/5659* (2013.01); *G01R 33/5605* (2013.01)

(58) Field of Classification Search
CPC .............. G01R 33/543; G01R 33/4835; G01R 33/5659; G01R 33/5605; G01R 33/5607; G01R 33/446; A61B 5/055
See application file for complete search history.

(56) References Cited

U.S. PATENT DOCUMENTS

| | | |
|---|---|---|
| 9,599,690 B2 | 3/2017 | Feiweier |
| 2013/0342207 A1 | 12/2013 | Keupp et al. |
| 2014/0253120 A1 | 9/2014 | Ugurbil et al. |
| 2018/0267120 A1 | 9/2018 | Li et al. |

(Continued)

FOREIGN PATENT DOCUMENTS

EP    2681578 A1    1/2014

OTHER PUBLICATIONS

Auerbach, Edward J., et al. "Multiband accelerated spin-echo echo planar imaging with reduced peak RF power using time-shifted RF pulses." Magnetic resonance in medicine 69.5 (2013): 1261-1267. (Year: 2013).*

(Continued)

*Primary Examiner* — Rishi R Patel
(74) *Attorney, Agent, or Firm* — Banner & Witcoff Ltd.

(57) ABSTRACT

A method for controlling a magnetic resonance imaging system, including: selecting a plurality of spatially non-selective initial RF-pulses each having a predefined pulse shape and a predefined frequency; determining a combined RF-pulse from the initial RF-pulses by choosing a time-offset comprising a relative application time-shift between the initial RF-pulses, wherein this time-offset is chosen such that the initial RF-pulses overlap; and including the combined RF pulse in a pulse sequence applied in a magnetic resonance imaging system.

14 Claims, 9 Drawing Sheets

(56) References Cited

U.S. PATENT DOCUMENTS

2019/0033408 A1    1/2019  Zeller

OTHER PUBLICATIONS

Melki P. et al., "Magnetization Transfer Effects in Multislice RARE Sequences", Magnetic Resonance in Medicine 24, pp. 189-195, 1992.
Malik, S. et al., "Steady?state imaging with inhomogeneous magnetization transfer contrast using multiband radiofrequency pulses", Magn Reson Med., 83:935-949, 2020.
Raja, A. et al., "Radiology Utilization in the Emergency Department: Trends of the last Two Decades", AJR Am J Roentgenol, 203(2): 355-360, doi: 10.2214/AJR.13.11892, 2014.
R.M. Henkelman et al: "Review Article: Magnetization transfer in MRI: a review" NMR in Biomedicine, NMR Biomed. 2001; 14, 57-64, received Feb. 18, 2000; revised Oct. 13, 2000, accepted Oct. 20, 2000; 2000.

\* cited by examiner

TSE (implicit MT)　　Single MT-preparation　　Multiple MT-preparations

METHOD AND SYSTEM FOR CONTROLLING A MAGNETIC RESONANCE IMAGING SYSTEM

TECHNICAL FIELD

The disclosure describes a method and a system for controlling a magnetic resonance imaging system ("MRI system"), especially for an optimized contrast preparation using multi-spectral, in particular spatially non-selective RF-pulses (radio frequency pulses).

BACKGROUND

The relevance of magnetic resonance (MR) imaging for clinical diagnosis is strongly linked to the versatility of available contrast-generating mechanisms. A subset of the latter requires spatially non-selective excitation of proton spins with a specific frequency characteristic. Such characteristic is e.g. a Magnetization transfer, chemically selective saturation or Chemical exchange saturation transfer.

A) Magnetization Transfer (MT)

The impact of Magnetization Transfer effects on standard MR imaging procedures is well known (see e.g. Melki and Mulkern: "Magnetization Transfer Effects in Multislice RARE Sequence", Magn. Reson. Med. 24:189; 1992). For example, each spatially selective RF-pulse which gets applied "on-resonance" from the perspective of spins in a desired slice location will (partially) saturate bound water protons in the surrounding volume. Thus, multi-slice imaging experiments with multiple spatially selective RF-pulses will often show tissue contrast with additional contributions from MT effects.

For the diagnosis of white matter lesions (e.g. Multiple Sclerosis), T2-FLAIR images with contributions from MT effects are often preferred by radiologists due to their clear depiction of conspicuous regions.

Given the rather long acquisition time and potentially high levels of the specific absorption rate (SAR) of Turbo spin echo (TSE) acquisitions, there is the need for alternative imaging techniques that can provide similar contrast in less time. Echoplanar imaging (single-shot ss-EPI or multi-shot techniques ms-EPI) allows fast acquisition of T2-FLAIR images, with a flexible trade-off between acquisition speed and image quality. This is highly desirable in applications which are time-critical, e.g. MR imaging in an emergency room, which is one of the fastest growing sectors in MR (see e.g. A. S. Raja et al.: "Radiology Utilization in the Emergency Department: Trends of the Past 2 Decades," Am. J. Roentgen., 203: 355-360; 2014).

Echoplanar imaging usually exhibits a limited amount of Magnetization Transfer contributions in its image contrast due to its small number of applied RF-pulses. Additional RF-pulses which get applied in dedicated "MT-preparation modules" can help to establish the desired contrast. However, utilization of currently available MT-preparation modules leads to RF-pulse sequences which disadvantageously suffer from long execution times, and/or high RF peak power demand.

After realizing the relevance of magnetization transfer for the contrast of MR-images, the idea to deliberately saturate protons from the bound water pool came up as an obvious application. Today, many sequences can be configured to apply an additional preparation module which enhances MT-effects.

Technically, an MT-preparation module can be rather simple: it contains a single, off-resonance, spatially non-selective RF-pulse with a rather high amplitude. Typically, a Gaussian pulse shape is used which provides a reasonable compromise between spectral selectivity and required RF power (see e.g. Henkelman et al.: "Magnetization Transfer in MRI: a Review", NMR in Biomed. 14:57; 2001). The frequency offset of the pulse is selected such that a decent saturation of bound water protons is obtained while still avoiding pre-saturation of the "on-resonant" protons to be imaged.

A non-selective RF-pulse affects all spins within the scanner. In contrast, with selective pulses one can e.g. choose to excite only the spins in a slice within an object in the scanner. Selective pulses are usually done by applying a magnetic field gradient throughout the volume. This gradient causes the protons to spin at different frequencies, depending on where they are along that gradient. By choosing the right frequency and bandwidth of the pulse, one can only excite specific spins along the gradient.

Applying MT-preparation pulses with multiple (off-resonance) frequencies simultaneously will generate stronger saturation effects within a given duration (see e.g. Malik et al.: "Steady-State Imaging with ihMT Contrast Using Multiband RF pulses", Magn.Reson.Med. 83:935; 2020). However, because realizing these pulses increases the RF peak amplitude demand, hardware limitations will restrict the applicability of this approach.

B) Chemically Selective Saturation (CS)

Chemically selective saturation can be used to suppress signal contributions of hydrogen atoms bonded to specific chemical compounds. For example, protons from hydrogen atoms bound to fat or silicone molecules exhibit different Lamor precession frequencies than those bound to water. By selectively exciting these spins with frequency-selective RF-pulses and by successively dephasing the generated transverse magnetization, it is possible to attenuate the corresponding signal contributions during the MR signal acquisition period of the imaging procedure.

However, in the state of the art, the saturation of multiple spin species with different frequencies or the combination of a chemically selective saturation pulse and an MT-preparation RF-pulse suffers from long preparation durations and/or high RF peak power demand.

C) Chemical Exchange Saturation Transfer (CEST)

Chemical exchange saturation transfer can be used to analyze the presence of specific chemical compounds in the bound water pool, which are not directly accessible by MR imaging due to their short T2 relaxation times. Essentially, this requires the saturation of specific frequency bands with frequency-selective RF-pulses in a preparation step, followed by the MR signal acquisition.

In the state of the art, the selective saturation of multiple bands and the combination of a CEST-preparation with an MT-preparation or a CS-preparation suffers from long preparation durations and/or high RF peak power demand.

A spatially non-selective saturation of a specific frequency band, which constitutes the basis of a CS- or a CEST-preparation, respectively, might get realized by an RF-pulse which applies a desired excitation angle of the magnetization (e.g. a flip by 90° from the longitudinal direction into the transverse plane) within a defined spectral band. For example, a Gaussian or a Sinc-type pulse shape can be used for this purpose: the frequency offset and the spectral width are selected such that the desired saturation band is covered.

If a specific contrast preparation requires the saturation of multiple non-contiguous frequency bands before acquiring the MR signal, known techniques apply the corresponding RF-pulses successively, which extends the duration considerably. Applying these RF-pulses simultaneously will on the other hand increase the RF peak amplitude demand.

SUMMARY

It is the object of the present disclosure to improve the known systems, devices and methods to facilitate an improvement in controlling a magnetic resonance imaging system, especially for an optimized contrast preparation using multi-spectral, in particular spatially non-selective RF-pulses.

A method according to the disclosure for controlling a magnetic resonance imaging system, especially for an optimized contrast preparation using multi-spectral, in particular spatially non-selective RF-pulses (radio frequency pulses) comprises the following steps:

Selecting a multiplicity of spatially non-selective initial RF-pulses (at least two) each having a predefined pulse shape (also designated as "envelope") and a predefined frequency. An initial RF-pulse is the basic building block of a shifted multi-band RF-pulse. It has an amplitude that is below a maximum capacity of the MR-scanner, a finite duration T, and will excite a single predefined frequency band. The initial RF-pulse is spatially non-selective what means that all spins within the imaging volume in the scanner are affected by an initial RF-pulse. Spatially non-selective pulses don't use a gradient when they are applied and thus affect all spins within the scanner. Technically, "spatial non-selective" means that no magnetic field gradient (a slice selection gradient) is switched on while the RF-pulse gets applied.

The initial RF-pulses may also be designated as "sub-pulses" or "basic-pulses", since they are the basis for a resulting "combined RF-pulse" which is one goal of the disclosed subject matter. The initial RF-pulses are those pulses that are applied for spatially non-selective contrast preparation. The pulse shape as well as the frequency of the initial RF-pulses depend on the desired examination, e.g. magnetization transfer, chemically selective saturation or chemical exchange saturation transfer. The initial RF pulses themselves are well known in the state of the art e.g. a Gaussian or a Sinc-type pulse shape. Preferred envelopes are for example, pulse shapes $B_1(t)$ with the maximum amplitude A, given by the formula $$B_1(t) = A e^{-(t-t_0)^2/\sigma^2} e^{i\Delta\omega t} \quad (1)$$

or $$B_1(t) = A \sin\left(\frac{t-t_0}{\sigma}\right) \frac{\sigma}{t-t_0} e^{i\Delta\omega t} \quad (2)$$

with the time t, the central time-point $t_0$, the temporal width parameter $\sigma$ and the frequency offset $\Delta\omega$ (more exactly the frequency offset is $\Delta\omega/2\pi$). However, the initial RF-pulse envelope is not limited to a Gaussian shape or Sinc-shape, but can also be e.g. a sinus lobe, or a shape with or without apodization.

The frequency $\omega=\omega_0+\Delta\omega$ is the center frequency of the band which should get excited to generate the desired contrast. The central frequency $\omega_0$ is the on-resonance frequency (Larmor precession frequency) of the proton spins in the MR magnet. The frequency offset $\Delta\omega$ determines the center of the desired frequency band. It should be noted that in MRI all applied RF-pulses get modulated on a carrier ("base frequency"; e.g. the average Larmor precession frequency of the spins within the imaging volume) that is $\omega_0$. For the sake of clarity, the constant value $e^{i\omega_0 t}$ is not included in the equations in this description, because the relevant part of these equations for this disclosure is the frequency offset $\Delta\omega$. This is well known by everyone skilled in the art.

There could be several pulses with different frequencies to excite different bands. For saturation purposes (if the transverse magnetization which is generated by the RF-pulses is not used for imaging purposes), the relative phase of the initial RF-pulses can be a free parameter which might e.g. get optimized to minimize the peak amplitude of the combined RF-pulse.

Determining a combined RF-pulse from the initial RF-pulses by choosing a time-offset (relative application time-shift and preferably also a phase-shift) between initial RF-pulses, wherein this time-offset is chosen such that the initial RF-pulses overlap. The relative application time-shift in the time-offset determines the temporal overlap of the initial RF-pulses.

The present disclosure is not only advantageous for amplitude modulated RF-pulses, but also for frequency or phase modulated RF-pulses (with complex-valued envelopes). An amplitude modulated RF-pulse exhibits a temporal variation of the (real-valued) amplitude A(t) and a constant (center) frequency offset $\Delta\omega$, i.e., $B_1(t)=A(t)\cdot e^{i\Delta\omega t}$, a frequency modulated RF-pulse exhibits temporal variations of the frequency, $\omega'$ (t) as well, e.g. where $B_1(t)=A(t)\cdot e^{i\Delta\omega t}\cdot e^{i\omega'(t)t}$, wherein this is equivalent to a temporal phase variation: $B_1(t)=A(t)\cdot e^{i\Delta\omega t}\cdot e^{i\varphi(t)}$. The described technique can be applied to any of these RF-pulses. The time-offset, however, always comprises the relative application time-shift. Here, A(t) is the amplitude modulation function and $\omega'$ (t) is the frequency modulation function, whereas $\varphi(t)=\omega'$ (t)·t is the equivalent phase modulation. As already said before, $\Delta\omega$ is the predefined frequency offset.

However, the time-offset cannot be chosen arbitrarily, since the pulses temporally shifted by the time-offset must overlap. That means that the time-offset must be smaller than the duration of the shifted pulses, or in other words: the time-offset between two initial RF-pulses is such that the (especially all) initial RF-pulses are arranged such that there is always a temporal overlap of the initial RF-pulses having a non-empty set of time points where an RF-contribution of both initial RF-pulses is non-zero. In short: "overlap" means that there is no time gap between the initial RF-pulses or, respectively, that a pulse is applied before the preceding pulse ends.

There should be chosen a time-offset between all initial RF pulses so that the initial RF-pulses have a time-shift to another. When there are three or more initial RF-pulses, the time-offset between these RF-pulses may all be the same or there may be (partly) different time-offsets. It is preferred that two initial RF-pulses do not overlap completely so that the maximum amplitude should not exceed a certain maximum, given by limits of the MR-scanner, the examination boundaries or a specific absorption rate.

Concerning the maximum, it should be noted that an MR-scanner cannot generate pulses with an amplitude exceeding a certain, scanner-specific value. Additionally, there are safety limits which prevent the scanner from generating sequences of pulses that exceed a SAR level. Since the SAR level increases with pulse amplitude, the maximum allowed pulse amplitude is also limited by this SAR safety limit. When designing pulses, the person may choose to use these limits or may specify another limit, e.g. a lower limit.

Including the combined RF pulse in a pulse sequence,
and preferably: Applying the pulse sequence in a magnetic resonance imaging system.

How to include a pulse in a pulse sequence and how to apply the pulse sequence is well known in the art.

It is clear that in the case in which multiple different combined RF-pulses are desired for different parts of the pulse sequence, the method can be applied for determining each of the combined RF-pulses from respective initial RF-pulses.

Thus, the core idea of the disclosed subject matter is the use of partially overlapping RF-pulse shapes of spatially non-selective RF-pulses. By appropriately selecting the overlap, the maximum RF-amplitude will not exceed the properties of an MRI-system and the duration of the MT-preparation module will be reduced (compared to a corresponding conventional sequence of single-band RF-pulses). At the same time, the frequency spectrum will still exhibit desired properties, with its maximum(s) at the given frequency offset(s).

Thus, a desired amount of MT contributions can be generated by dedicated preparation modules. Compared to standard preparation schemes, this method can generate similar MT-effects in a shorter duration and/or using lower RF peak amplitudes.

The disclosed subject matter can e.g. be used to enhance MT contrast in weighted imaging (such as FLAIR contrast). However, the overlapping pulses may also be used in quantitative imaging where multiple different MT preparations are used to quantify tissue properties related to MT (e.g. fractional pool sizes or exchange rates).

If the actual shape of the frequency spectrum doesn't matter (as long as there is negligible pre-saturation of magnetization which shall get used for imaging purposes), it is possible to apply a series of preparation pulses, e.g. in order to amplify the magnetization transfer effect. The method according to the disclosure enables a compression of such a train of RF-pulses, thus shortening the required preparation duration. For example, a combined RF-pulse consists of a series of N sub-pulses with identical shapes (e.g. Gaussian) and durations (e.g. 5ms), but especially alternating frequency offsets (e.g. +/−1200 Hz). It is preferred that each succeeding sub-pulse starts before the preceding sub-pulse ends. This ensures that sub-pulses with identical frequency offset do not overlap, which preserves a desirable frequency spectrum.

A system according to the disclosure for controlling a magnetic resonance imaging system comprises the following components:

A selection unit designed for selecting a multiplicity of spatially non-selective initial RF-pulses each having a predefined pulse shape and a predefined frequency.

This selection unit may be designed for receiving data about initial RF-pulses, especially mathematical functions or emission patterns of initial RF-pulses, e.g. manually chosen or chosen by an external device. This received data defines the selected initial RF-pulses. However, the selection unit may also receive data about an examination and an appropriate protocol and may automatically select initial RF-pulses from the protocol.

A determination unit designed for determining a combined RF-pulse from the initial RF-pulses by choosing a time-offset comprising a relative application time-shift and preferably also a phase-shift between the initial RF-pulses, wherein this time-offset is chosen such that the initial RF-pulses overlap.

A sequence control unit designed for including the combined RF pulse in a pulse sequence. Such unit is known from the prior art.

A radio-frequency transmission device designed for applying the pulse sequence in a magnetic resonance imaging system. Such unit is known from the prior art.

The determination unit of the system is preferably designed to perform preferred method steps of the method according to the disclosure concerning special computations and/or algorithms for the combined RF-pulse. For that, the determination unit preferably comprises a computation module designed to achieve this purpose.

A control device according to the disclosure for controlling a magnetic resonance imaging system comprises a system according to the disclosure. Alternatively or additionally it is designed to perform the method according to the disclosure. The control device may comprise additional units or devices for controlling components of a magnetic resonance imaging system, e.g. a sequence control unit for measurement sequence control, a memory, a radio-frequency transmission device that generates, amplifies and transmits RF pulses, a gradient system interface, a radio-frequency reception device to acquire magnetic resonance signals and/or a reconstruction unit to reconstruct magnetic resonance image data.

A magnetic resonance imaging system comprising a control device according to the disclosure.

Some units or modules of the system or the control device mentioned above can be completely or partially realized as software modules running on a processor of a system or a control device. A realization largely in the form of software modules can have the advantage that applications already installed on an existing system can be updated, with relatively little effort, to install and run these units of the present application. An object of the disclosure is also achieved by a computer program product with a computer program that is directly loadable into the memory of a device of a system or a control device of a magnetic resonance imaging system, and which comprises program units to perform the steps of the inventive method when the program is executed by the control device or the system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a control device or a system. A processor unit can comprise one or more microprocessors or their equivalents.

Particularly advantageous aspects and features of the disclosure are given by the dependent claims, as revealed in the following description. Features of different claim categories may be combined as appropriate to give further aspects not described herein.

According to a preferred method, the initial RF-pulses are designed for spatially non-selective excitation of proton spins, preferably for pulse sequences designed for magnetization transfer, chemically selective saturation or chemical exchange saturation transfer.

According to a preferred method, at least two of the initial RF-pulses have a different frequency, wherein the difference between the frequencies of the pulses is preferably more than 50 Hz, especially more than 100 Hz, wherein depending on the strength of the main magnetic field and the purpose it could also be more than 1 kHz. Preferably, two initial RF-pulses have separate (non-overlapping) frequency bands. This means that the difference between the frequencies is preferably larger than the sum of the half bandwidth of either pulse. Thus, different initial RF-pulses have preferably different frequency offsets, wherein the frequency offset preferably depends on the pulse shape.

The frequency offsets may be bigger than 1 kHz for Gaussian pulses or appropriate for non-selective excitations or saturations of specific frequency bands. For example, a simultaneous chemically selective saturation of fat protons (with a chemical shift of e.g. 3 ppm resulting in an offset of 380 Hz at 3 T) and of silicone protons (e.g. 5.5 ppm resulting in an offset of 700 Hz at 3 T) requires the application of two RF-pulses with the desired frequency offsets and bandwidths, e.g. using a Sinc envelope (see equation 2).

It is clear that when applying more than two initial RF-pulses, it is possible (and depending on the case preferred) to use more than two different off-resonance frequencies. While this changes the frequency spectrum, it allows an even higher compression, without overlapping sub-pulses with identical frequency offset.

According to a preferred method, the time-offset is chosen such that an absolute value of a maximum of the combined RF-pulse does not exceed a predefined maximum RF-intensity (the absolute value of the maximum amplitude) being lower than the maximum applicable RF-intensity of the magnetic resonance imaging system. It is preferred that the absolute value of the maximum RF intensity of the combined RF-pulse is not exceeding the absolute value of a maximum RF-intensity of the initial RF-pulses.

According to a preferred method, the pulse shape B1(t) of a number of initial RF-pulses with the amplitude A, the center of support of the pulse (often the time of the maximum) $t_0$, the frequency offset $\Delta\omega/2\pi$ and the temporal width parameter $\sigma$ follows the formula:

$$B_1(t) = Ae^{-(t-t_0)^2/\sigma^2}e^{i\Delta\omega t} \text{ (Gaussian pulse) or}$$

$$B_1(t) = A\,\text{sin}\left(\frac{t-t_0}{\sigma}\right)\frac{\sigma}{t-t_0}e^{i\Delta\omega t} \text{ (Sinc pulse)}.$$

According to a preferred method, the pulse shape and/or the duration T of a number of initial RF-pulses is identical, wherein these initial RF-pulses preferably have different frequency offsets. The support of the pulse $t_0$ is defined as the set of time points for which the pulse takes on non-zero values. The center of this set would be defined as the average of the maximum and minimum times in the support. Concerning the duration T, $t_0$ lies right in its center.

According to a preferred method, two initial RF-pulses are arranged such that there is always a temporal overlap of the initial RF-pulses having a non-empty set of time points where an RF-contribution of both initial RF-pulses is non-zero. This means that there is always a region where non-zero contributions of RF pulses are added. In other words, there is always a non-empty set of time points common to the support of each RF pulse, where the "support" of a RF pulse is the set of time points for which that pulse takes on non-zero-values.

According to a preferred method, the time-offset is chosen such that a minimal temporal shift between two initial RF-pulses is determined, preferably where the absolute value of a maximum of the combined RF-pulse does not exceed the predefined maximum RF-intensity. This is preferably done with the following steps:

a) providing the pulse shapes of the initial RF-pulses,
b) providing a predefined minimal test-offset comprising a time-shift and preferably also a phase-shift, especially with the value zero,
c) providing a predefined maximum RF-intensity,
d) calculating a summed RF-pulse of the initial RF-pulses, where at least one initial RF-pulse is temporally shifted with the test-offset,
e) comparing the absolute value of the maximum of the summed RF-pulse with a predefined maximum RF-intensity and if the absolute value of the maximum of the summed RF-pulse exceeds the maximum RF-intensity, increase the test-offset between two of the initial RF-pulses with a predefined temporal value and repeat steps d) to e), and if it does not, take the actual summed RF-pulse as combined RF-pulse, wherein the steps are performed until the time-shift of the test-offset exceeds the length of the initial RF-pulses such that they do not overlap any more.

According to a preferred method, in the course of increasing the test-offset, a time-shift is increased by a predefined positive or negative shift and preferably also a phase-shift is increased by a positive or negative shift until it exceeds the value of $2\varphi$. It is preferred that if both shifts are applied, then one, especially the phase-shift, is applied in an inner loop and the other is applied in an outer loop (while it is clear that before starting, the inner loop is always reset in its initial condition before starting).

A preferred algorithm that will be advantageous for symmetric sub-pulses (initial RF-pulses). The algorithm uses a time-shift $\Delta t$, a phase-shift $\Delta\varphi$, functions F(t) and G(t) for two (possibly different) initial RF-pulses (preferably spatially non-selective RF-pulses used for contrast preparation with separate, non-overlapping frequency bands) with the durations $T_F$ resp. $T_G$, incrimination values $\Delta t_{inc}$ and $\Delta\varphi_{inc}$ and the maximum RF-pulse amplitude $RF_{max}$ (may be max{F(t)} in absolute values). The algorithm may also be used for asymmetric sub-pulses, wherein in this case it would be preferred to perform it twice with a negated $\Delta t$ in the second run. After the two runs, the value of $\Delta t$ with the smallest magnitude and the corresponding $\Delta\varphi$ would be selected. The preferred algorithm comprises the steps:

1. $\Delta t = 0$
2. $\Delta\varphi = 0$
3. $F_{sum}(t) = F(t) + G(t-\Delta t) \cdot e^{i\Delta\varphi}$
4. Max $(|F_{sum}(t)|) \leq RF_{max}$ for all $t \in \{t : |F_{sum}(t)| > 0\}$ ?
   Yes: end – solution found.
5. $\Delta\varphi = \Delta\varphi + \Delta\varphi_{inc}$
6. $\Delta\varphi < 2\pi$ ?
   Yes: continue with step 3.
7. $\Delta t = \Delta t + \Delta t_{inc}$
8. $|\Delta t| < (T_F/2 + T_G/2)$ ?
   Yes: continue with step 2.
   No: End – no solution found.

The algorithm above refers to arbitrary (and possible different) initial RF-pulse shapes F(t) and G(t), where G(t) already may include a frequency shift. For example, for amplitude-modulated RF-pulses (i.e. real-valued amplitudes), $F(t)=A1(t)\cdot e^{i\Delta\omega_1 t}$ and $G(t)=A2(t)\cdot e^{i\Delta\omega_2 t}$. The amplitude modulation functions A1(t) and A2(t) can be different or identical. Although there is a chance that the algorithm may find a time offset at $\Delta t=0$, it is very improbable and $\Delta t$ is usually greater than 0. The same ($\Delta t$ usually greater than 0 for choosing the combined RF-pulse) is valid for the next examples as well. The Value $\Delta t_{inc}$ may depend on the scanner hardware (e.g. the digital-analog-converters), wherein it may be a certain minimum time-shift step, e.g. 100 ns or 10 ns or 1 ns.

A preferred simplified algorithm with no contribution of the phase may read:

1. $\Delta t = 0$
2. $F_{sum}(t) = F(t) + G(t-\Delta t)$
3. Max $(|F_{sum}(t)|) \le RF_{max}$ for all $t \in \{t : |F_{sum}(t)| > 0\}$ ?
   Yes: end − solution found.
4. $\Delta t = \Delta t + \Delta t_{inc}$
5. $|\Delta t| < (T_F/2 + T_G/2)$ ?
   Yes: continue with step 2.
   No: End − no solution found.

A preferred more simplified algorithm with two identical initial RF-pulses may read:

1. $\Delta t = 0$
2. $F_{sum}(t) = F(t) + F(t-\Delta t)$
3. Max $(|F_{sum}(t)|) \le RF_{max}$ for all $t \in \{t : |F_{sum}(t)| > 0\}$ ?
   Yes: end − solution found.
4. $\Delta t = \Delta t + \Delta t_{inc}$
5. $\Delta t < T_F$ ?
   Yes: continue with step 2.
   No: End − no solution found.

Although applying multi-band initial RF-pulses (sub-pulses) with identical shapes and/or amplitudes is desirable, one might envision using a different shape (e.g. Gaussians with different temporal width parameters) and/or a different amplitude for each of them. A generalized algorithm to calculate an optimized RF-pulse shape consisting of N sub-pulses with shapes $F_i(t)$ might use a numerical optimization to find the shortest composite RF-pulse which complies with RF peak power limitations:

Find time-offsets $\{\Delta t_i, \Delta\phi_i\}$ with $i \in \{1 \ldots N\}$ which realize a minimum value of $(\max\{t: |F_{sum}(t)|>0\} - \min\{t: |F_{sum}(t)|>0\})$, such that the magnitude of the summed RF-pulse $F_{sum} = \Sigma_{i=1 \ldots N} F_i(t-\Delta t_i) \cdot \exp(i\Delta\phi_i)$ is less than $RF_{max}$ for all $t \in \{t: |F_{sum}(t)|>0\}$. Without loss of generality, one might set $\Delta t_1 = 0$ and $\Delta\phi_1 = 0$ at the start of the respective loop.

Adding the constant phase $\exp(\Delta\phi_i)$ to each of the sub-pulses will not affect the MT-, CS- or CEST-properties but might help to reduce the maximum required RF amplitude.

In a preferred system according to the disclosure, components of the system are part of a data-network, wherein preferably the data-network and a medical imaging system (i.e. the magnetic resonance imaging system which provides image data) are in data-communication with each other, wherein the data-network preferably comprises parts of the internet and/or a cloud-based computing system, wherein preferably the system according to the disclosure or a number of components of this system is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved by means of data interfaces and/or data transmission protocols.

In the context of "cloud computing", in a preferred aspect of the method according to the disclosure, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred aspect of the system according to the disclosure, the abovementioned units are present on the "cloud" side. A preferred system further comprises, a local computing unit connected to the system via a data channel (e.g. a data-network, particularly configured as RIS or PACS). The local computing unit includes at least one data receiving interface to receive data. Moreover, it is preferred if the local computer additionally has a transmission interface in order to send data to the system.

Other objects and features of the present disclosed subject matter will become apparent from the following detailed descriptions considered in conjunction with the accompanying drawings. It is to be understood, however, that the drawings are designed solely for the purposes of illustration and not as a definition of the limits of the disclosure.

BRIEF DESCRIPTION OF THE DRAWINGS

In the diagrams, like numbers refer to like objects throughout. Objects in the diagrams are not necessarily drawn to scale.

DETAILED DESCRIPTION

Figure 1:
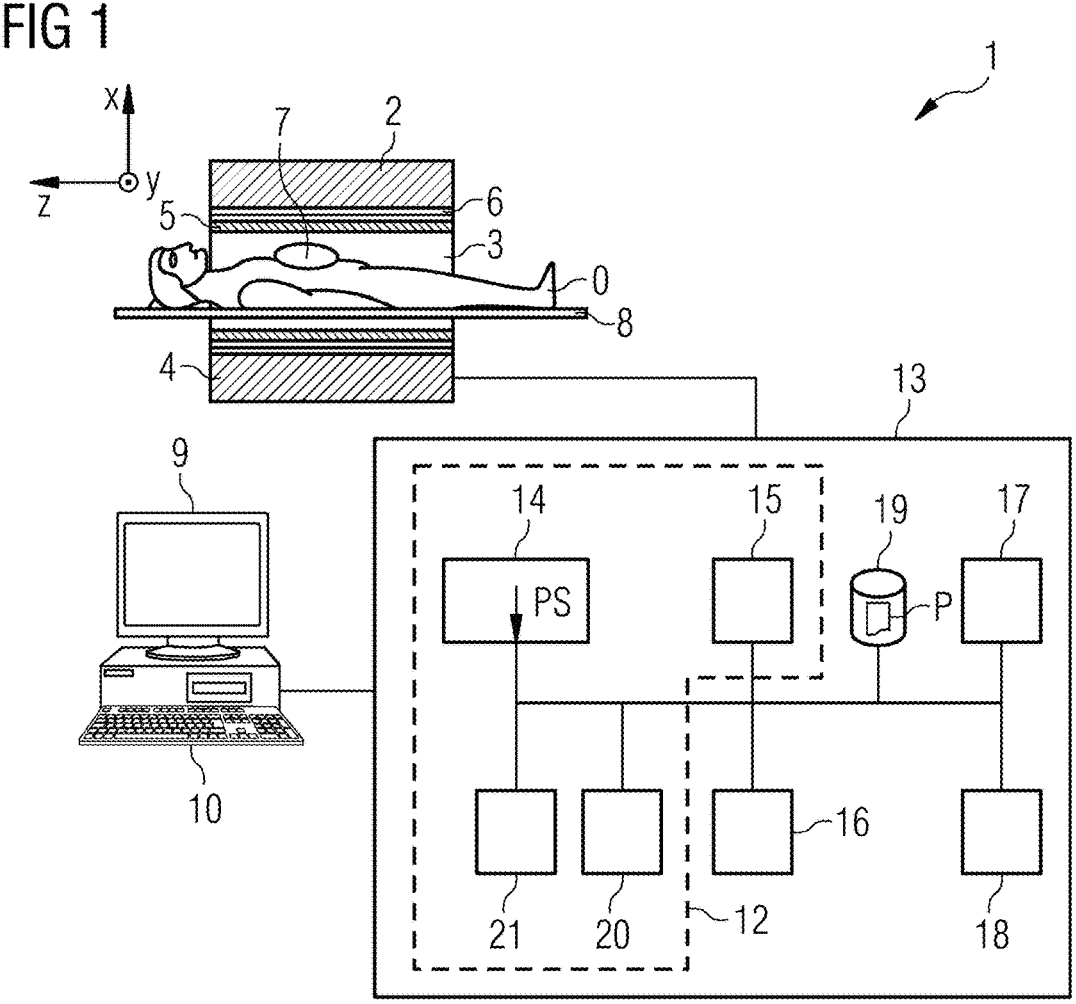
FIG. 1 shows a simplified MRI system according to an aspect of the disclosure.

FIG. 1 shows a schematic representation of a magnetic resonance imaging system 1 ("MRI-system"). The MRI system 1 includes the actual magnetic resonance scanner 2 (data acquisition unit) 2 with an examination space 3 or patient tunnel in which a patient or test person is positioned on a driven bed 8, in whose body the actual examination object is located.

The magnetic resonance scanner 2 is typically equipped with a main field magnet system 4, a gradient system 6 as well as an RF transmission antenna system 5 and an RF reception antenna system 7. In the shown exemplary aspect, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The main field magnet system 4 is preferably designed that at least two slices can be recorded. It here is designed in a typical manner so that it generates a main magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central control device 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence PS or, respectively, a series of multiple pulse sequence PS to acquire magnetic resonance images of the slices within a measurement session. For example, such a series of pulse sequence PS can be predetermined within a measurement or control protocol P. Different control protocols P for different measurements or measurement sessions are typically stored in a memory 19 and can be selected by and operator (and possibly modified as necessary) and then be used to implement the measurement.

To output the individual RF pulses of a pulse sequence PS, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence PS.

Moreover, the control device 13 has a radio-frequency reception device 17 (likewise communicating with the sequence control unit 14 in a suitable manner) in order to acquire magnetic resonance signals (i.e. raw data) for the individual measurements, which magnetic resonance signals are received in a coordinated manner from the RF reception antenna system 7 within the scope of the pulse sequence PS.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started by means of the input unit (possibly in combination with the display unit 9), and in particular suitable control protocols can be selected (and possibly modified) with suitable series of pulse sequence PS as explained above.

The control device 13 comprises a system 12 designed to perform the method according to the disclosure. This system 12 comprises the following components that may appear to be software modules.

A selection unit 20 selects a number of initial RF-pulses each having a predefined pulse shape and a predefined frequency. This can be achieved when an examination is pending and a protocol P is chosen for this examination. In this exemplary protocol P there is a list of the initial RF-pulses P1, P2 that have to be applied during this examination. Thus, the protocol can easily be parsed for RF-pulses following each other and these RF-pulses can be selected as the initial RF-pulses. However, usually the combination of initial RF-pulses would take place within the MR pulse sequence already (e.g. within the "MT-preparation" module or the "fat saturation" module of the software). By taking care of the combination at an early stage, the sequence already "knows" about the reduced time of this module and can thus e.g. allow the user to take advantage of a shorter measurement duration in the protocol setup before starting the scan.

A determination unit 21 combines the selected initial RF-pulses P1, P2 according to the special method (see e.g. FIG. 2) to a combined RF-pulse CP by choosing a time-offset comprising a relative application time-shift and especially also a phase-shift between the initial RF-pulses P1, P2, wherein this time-offset is chosen such that the RF-pulses P1, P2 overlap.

The system 12 according to the disclosure is here the sum of selection unit 20, determination unit 21, sequence control unit 14 and radio-frequency transmission device 15 as shown by the dashed frame.

The MRI system 1 according to the disclosure, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
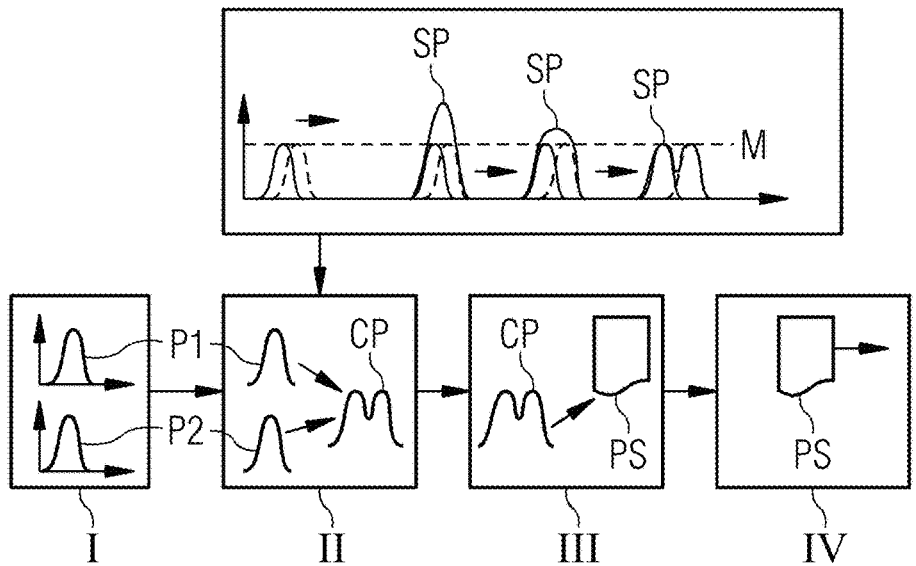
FIG. 2 shows a block diagram of the process flow of a preferred method according to the disclosure.

FIG. 2 shows a block diagram of the process flow of a preferred method according to the disclosure for controlling a magnetic resonance imaging system 1 (see. e.g. FIG. 1).

In step I, a multiplicity of initial RF-pulses P1, P2 is selected, each having a predefined pulse shape, here Gaussian, and a predefined frequency. The horizontal axis is the time and the vertical axis is the RF-intensity.

In step II, a combined RF-pulse CP is determined from the initial RF-pulses P1, P2 by choosing a time-offset comprising a relative application time-shift and especially also a phase-shift between the initial RF-pulses P1, P2 as can be seen in the box over step II. There are two initial RF-pulses P1, P2, one solid and one dashed, that are shifted in time until the maximum RF-intensity is not exceeding a predefined threshold for a maximum value M of the RF intensity. The sum SP of the two initial RF-pulses P1, P2 is shown as envelope over these two curves. The maximum value may be given by the maximum power of the scanner or chosen as the maximum of one of the initial RF-pulses P1, P2 as it is done here. At last, a time-shift and especially a phase-shift of the initial RF-pulses P1, P2 is chosen such that the RF-pulses overlap and the sum SP of the two initial RF-pulses P1, P2 does not exceed the maximum value M.

In step III, the combined RF pulse CP is included in a pulse sequence PS that is to be applied for the examination.

In step IV, the pulse sequence PS is applied in a magnetic resonance imaging system in the course of the actual examination.

Figure 3:
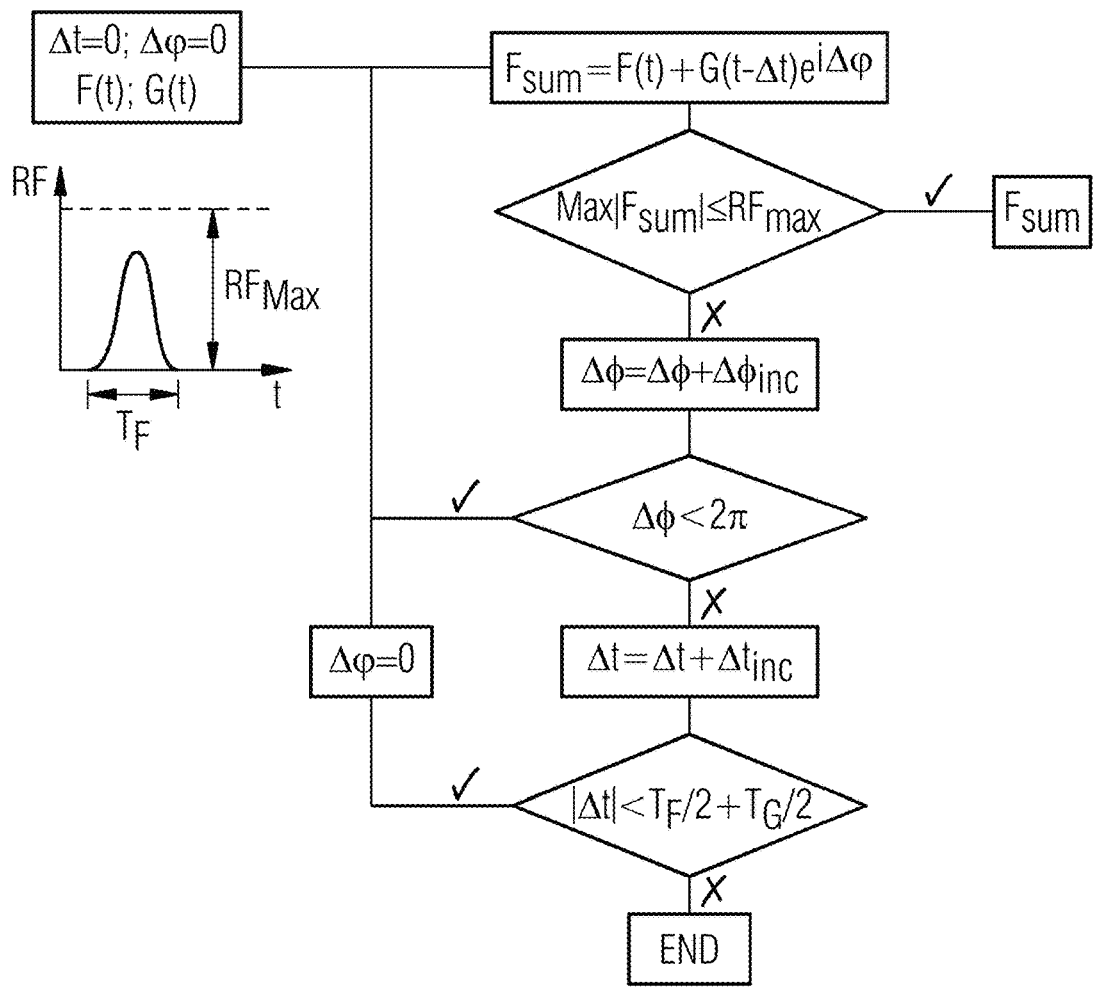
FIG. 3 shows a process flow of the determination of the combined RF-pulse.

FIG. 3 shows a process flow of the determination of the combined RF-pulse. It shows the following algorithm:

$$\Delta t=0; \Delta\varphi=0; \text{define initial pulse-functions F(t) and G(t).} \qquad 1.$$

A test-offset combined from the time-shift $\Delta t$ and the phase-shift $\Delta\varphi$ is set to zero. Furthermore, pulses F(t) and G(t), mathematical functions for the initial RF-pulses P1, P2, are defined, wherein the pulse shapes are the courses of the curves. F(t) and G(t) may have the same mathematical function (G=F) or different functions depending from the desired examination. The duration of the curves, i.e. the maximum time-shift where the curves do not overlap, is here given as $T_F$ and $T_G$.

Furthermore, the maximum RF-amplitude $RF_{max}$ is e.g. given by the properties of the machine or by other boundaries. It may be the absolute value of the maximum RF-amplitude of the initial RF-pulses P1, P2, however, in this example it is higher.

$$F_{sum}(t)=F(t)+G(t-\Delta t)\cdot e^{i\Delta\varphi} \qquad 2.$$

The (complex) sum function of F(t) and G(t) is calculated, where G(t) is shifted by the time-shift $\Delta t$ and the phase-shift $\Delta\varphi$. At first, these values are zero and the two functions overlap completely, this would probably result in a maximum amplitude that exceeds $RF_{max}$. Anticipating the following description, it is said that the following loops will always return to this point.

$$\text{Max}(|F_{sum}(t)|)\leq RF_{max}(\text{for all } t\in\{t: |F_{sum}(t)|>0\})? \qquad 3.$$

In this step it is determined whether the absolute value of the sum function $F_{sum}(t)$ exceeds the maximum value $RF_{max}$.

It should be noted that the curves may have positive and negative values, since RF-pulses may have positive or negative amplitudes. The determination is done over the whole duration of $F_{sum}(t)$, as long as this function is not zero.

In the case that $\text{Max}(|F_{sum}(t)|)\leq RF_{max}$, a solution is found and the combined RF-pulse CP is $F_{sum}$. The algorithm is stopped then and the combined RF-pulse CP is included into the pulse sequence PS (see above step III).

In the case, $\text{Max}(|F_{sum}(t)|)$ exceeds $RF_{max}$, the algorithm proceeds.

$$\Delta\varphi=\Delta\varphi+\Delta\varphi_{inc}. \qquad 4.$$

In this inner loop, the phase-shift $\Delta\varphi$ is incriminated by a predefined incrimination step $\Delta\varphi_{inc}$.

$$\Delta\varphi<2\pi? \qquad 5.$$

As long as $\Delta\varphi<2\pi$, the algorithm returns to step 2 (calculation of $F_{sum}$ with the incriminated phase-shift $\Delta\varphi$). Since it does not make sense to incriminate a phase-shift more than $2\pi$, the loop ends if $\Delta\varphi$ is equal or bigger than $2\pi$ and the algorithm proceeds with step 6.

It should be noted that a phase-shift is not always necessary or desired and only a time-shift should be performed. In this case, this inner loop is not included into the algorithm (and the term $e^{i\Delta\varphi}$ is omitted as well or set to 1).

$$\Delta t=\Delta t+\Delta t_{inc}. \qquad 6.$$

In this outer loop, the time-shift $\Delta t$ is incriminated by a predefined incrimination step $\Delta t_{inc}$. This value may depend on the scanner hardware (e.g. the digital-analog-converters). The value $\Delta t_{inc}$ may be a certain minimum time-shift step, e.g. 100 ns or 10 ns or 1 ns.

$$|\Delta t|<(T_F/2+T_G/2)? \qquad 7.$$

As long as there is an overlap between F and G, the algorithm returns to step 2 (calculation of $F_{sum}$ with the incriminated time-shift $\Delta t$). Before going to step 2, the phase-shift $\Delta\varphi$ is set to zero so that the inner loop may be performed again. When the absolute value $|\Delta t|$ exceeds the condition $T_F/2+T_G/2$, there is not severe overlap any more, and the loop ends. This would result in no result (what is a very rare end, e.g. only for rectangular functions F and G with $RF_{max}=\text{max } F$).

Figure 4:
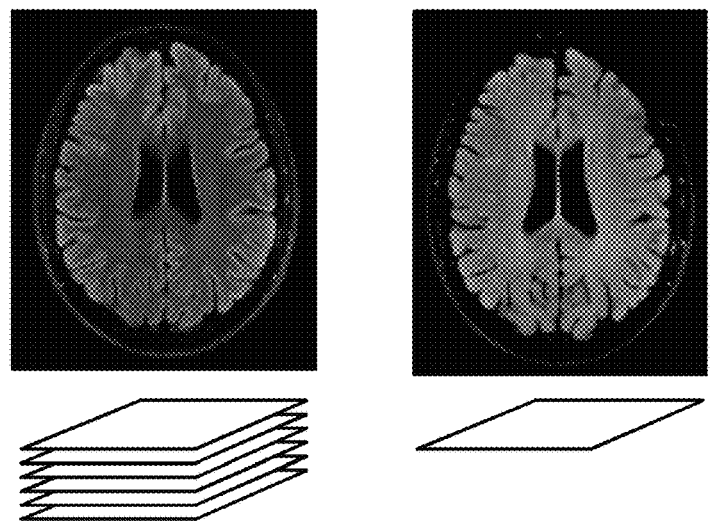
FIG. 4 shows two fluid-attenuated, T2-weighted Turbo spin echo images according to the state of the art.

FIG. 4 shows two fluid-attenuated (FLAIR), T2-weighted Turbo spin echo (TSE) images acquired with multiple slices (left) and a single slice only (right) according to the state of the art. These pictures demonstrate the relevance of Magnetization Transfer (MT) effects, wherein all other imaging parameters were kept identical. Compared to gray matter, white matter exhibits a considerable amount of bound water protons, mostly macromolecules within the myelin sheaths of axons. Saturation of the latter by the additional RF-pulses, and magnetization transfer between the water species yield additional attenuation of the white matter signal. In this T2-FLAIR example, the disclosure would enable the more advantageous ms-EPI acquisition to achieve contrast comparable to that of the established TSE technique.

Figure 5:
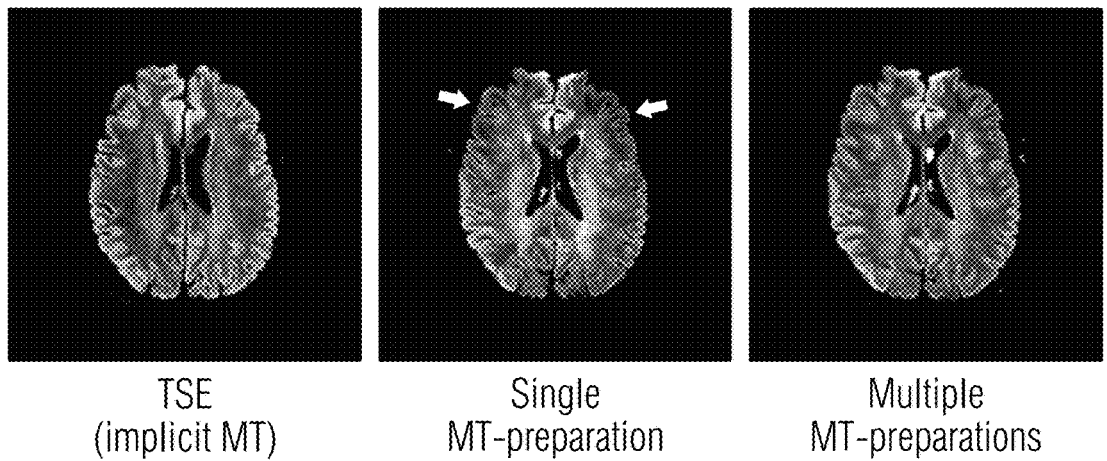
FIG. 5 shows the feasibility of MT-preparations to improve white matter/grey matter contrast in brain MRI according to the state of the art.

FIG. 5 shows examples demonstrating the feasibility of MT-preparations to improve the white matter to grey matter contrast in brain MRI. All images have been acquired with a fluid-attenuated (FLAIR) multi-shot echoplanar acquisition (ms-EPI), using various (standard) MT-preparation schemes. A corresponding T2-FLAIR TSE image is shown for reference.

It turns out that the amount of saturation in the bound water pool depends on the average of the squared applied B1 field amplitude <B1> (which is proportional to the applied RF power). The RF amplitude can be increased to enhance the effectiveness of the MT-preparation module, but hardware limitations restrict allowed levels of increase. Alternatively, repetitive applications of MT-preparation pulses yield enhanced MT-effects, at the expense of a longer duration.

For better understanding of the combined RF-pulses of the disclosed subject matter, some exemplary pulses of the state of the art are shown. The following FIGS. 6 to 14 show a number of different initial RF-pulses applied for various examinations. In these figures, the magnitude time course of a resulting pulse is shown in the upper left graph with arbitrary but compatible pulse magnitudes (a.u.=arbitrary units). On the lower left side, the time course of the pulse phase is shown and on the right the frequency distribution.

The single pulses have the temporal width parameter σ, the duration T (time-width at the base), a pulse energy E of $E = \int_{t_0-T/2}^{t_0+T/2} B_1^2(t) dt$ with the peak RF amplitude B1 and the duration T with its center $t_0$.

Figure 8:
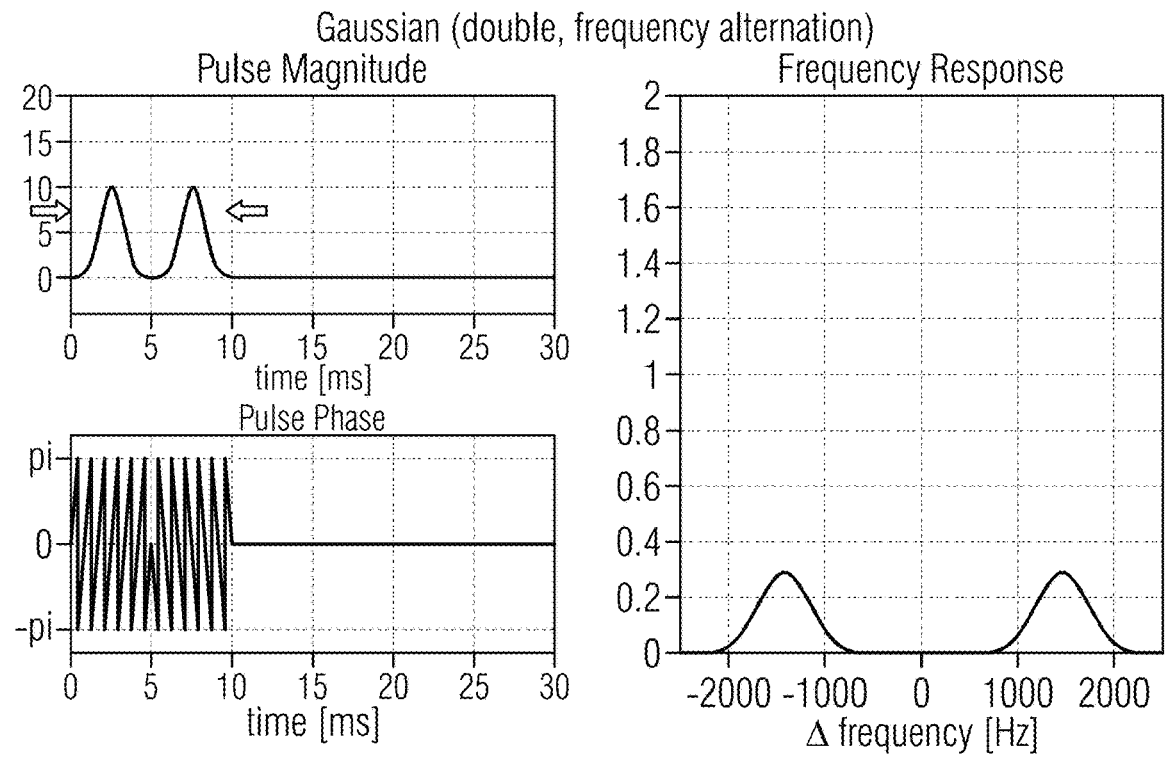
FIG. 8 shows an example for two adjacent Gaussian RF-pulses according to the state of the art.
Figure 9:
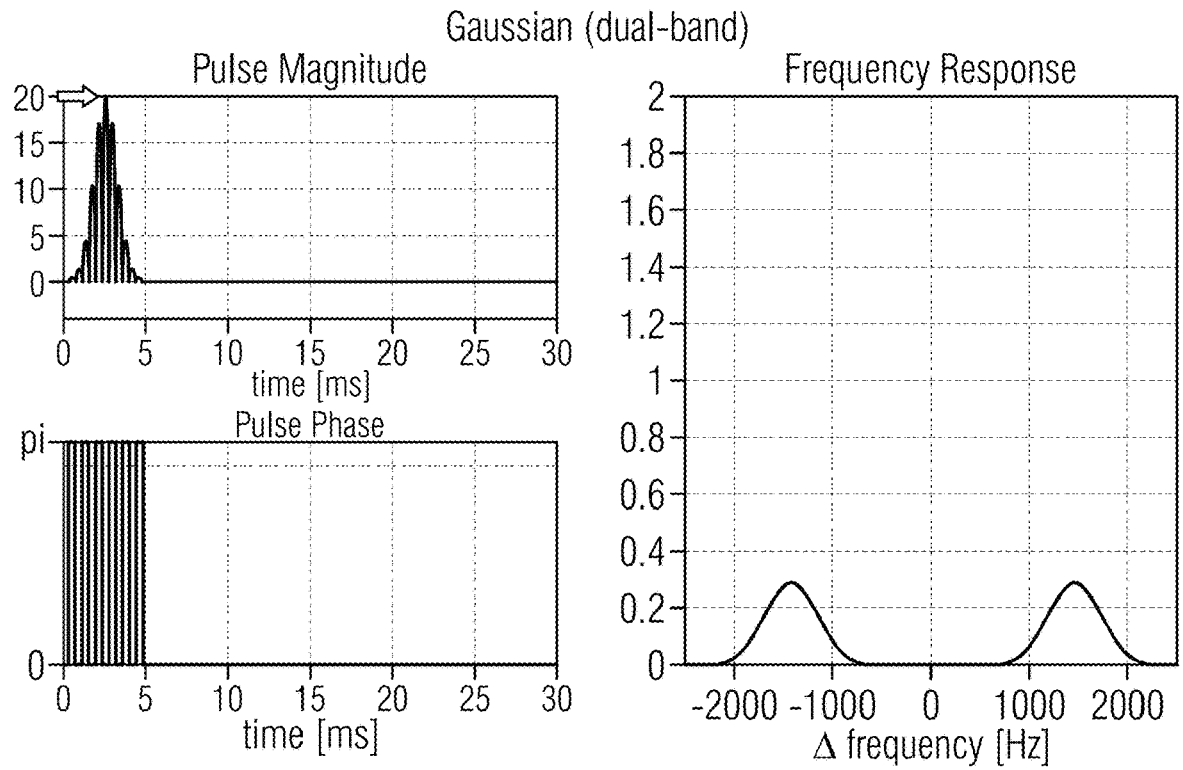
FIG. 9 shows an example for a Dual-band Gaussian RF-pulse according to the state of the art.
Figure 10:
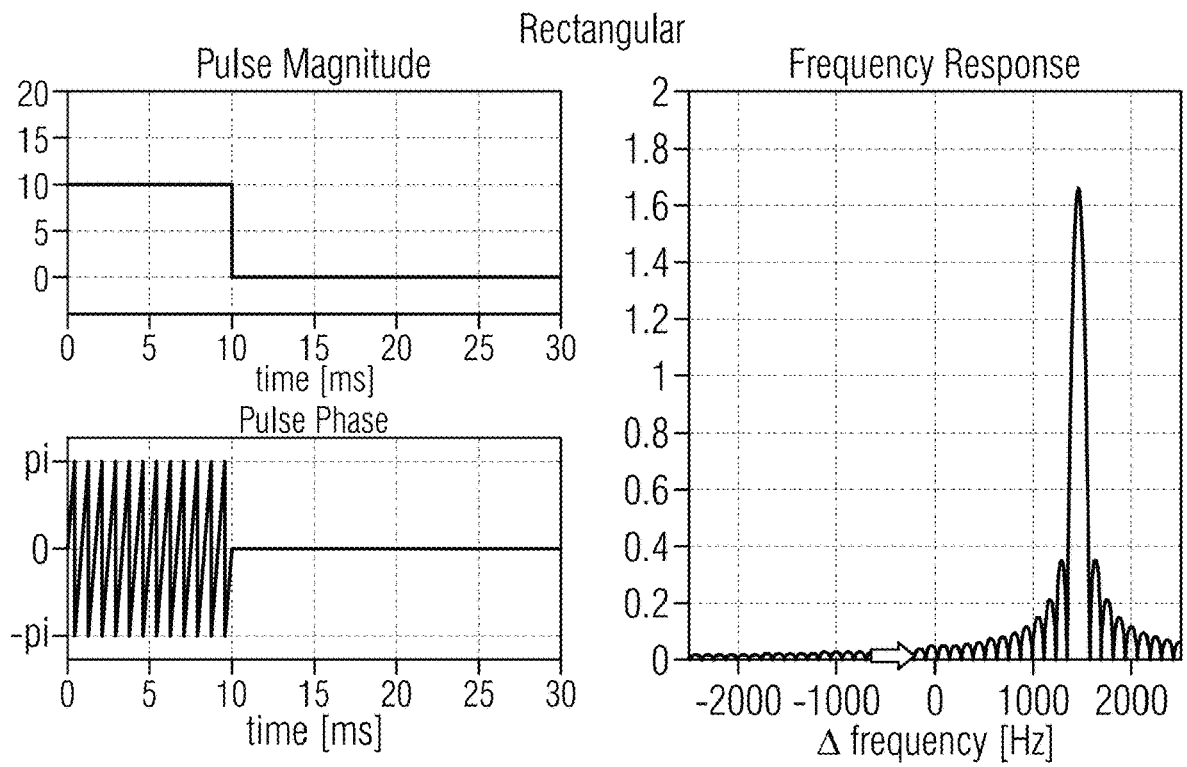
FIG. 10 shows an example for a rectangular RF-pulse according to the state of the art.
Figure 11:
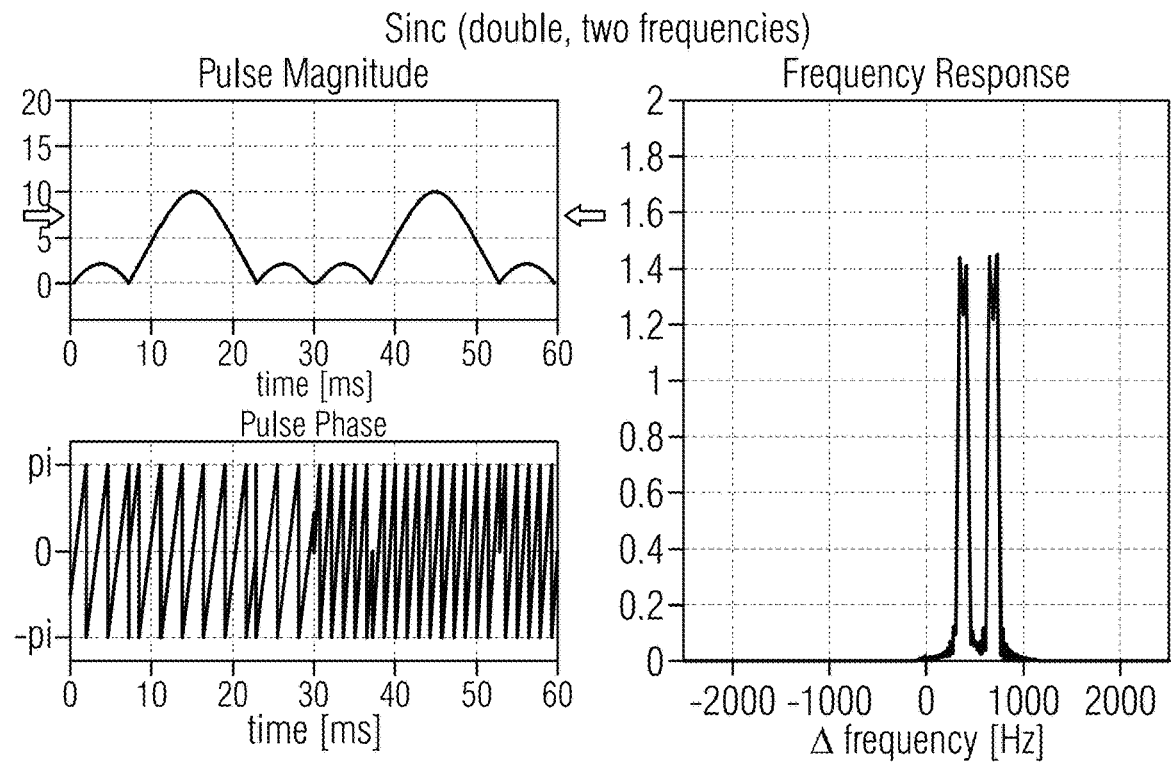
FIG. 11 shows an example for a double Sinc RF-pulse according to the state of the art.
Figure 12:
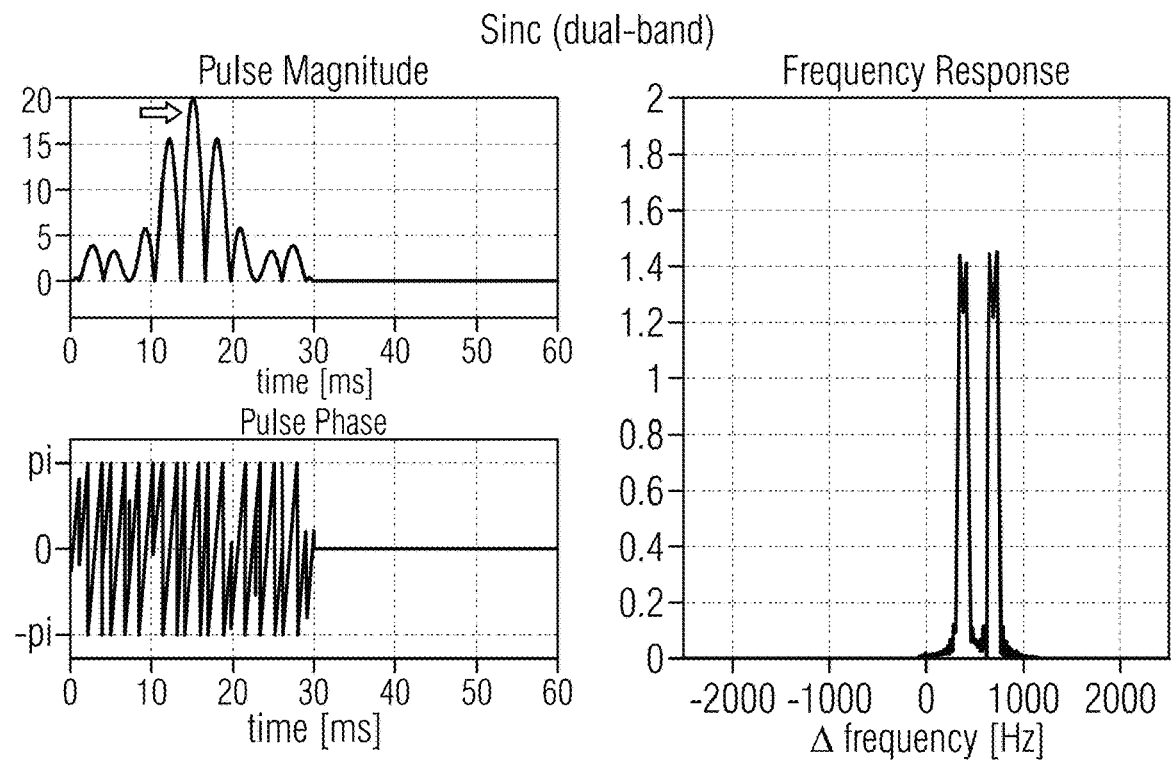
FIG. 12 shows an example for a Dual-band Sinc RF-pulse according to the state of the art.

In FIGS. 6 to 9, the pulses have a Gaussian envelope (see above equation 1) as their basis, FIG. 10 a rectangular pulse, FIGS. 11 and 12 a Sinc-RF-pulse envelope (see above equation 2) and FIGS. 13 and 14 again Gaussian envelopes.

$$\text{Gaussian envelope: } B_1(t) = Ae^{-(t-t_0)^2/\sigma^2} e^{i\Delta\omega t} \quad (1)$$

$$\text{Sinc RF-pulse envelope. } B_1(t) = A \sin\left(\frac{t-t_0}{\sigma}\right) \frac{\sigma}{t-t_0} e^{i\Delta\omega t} \quad (2)$$

Figure 6:
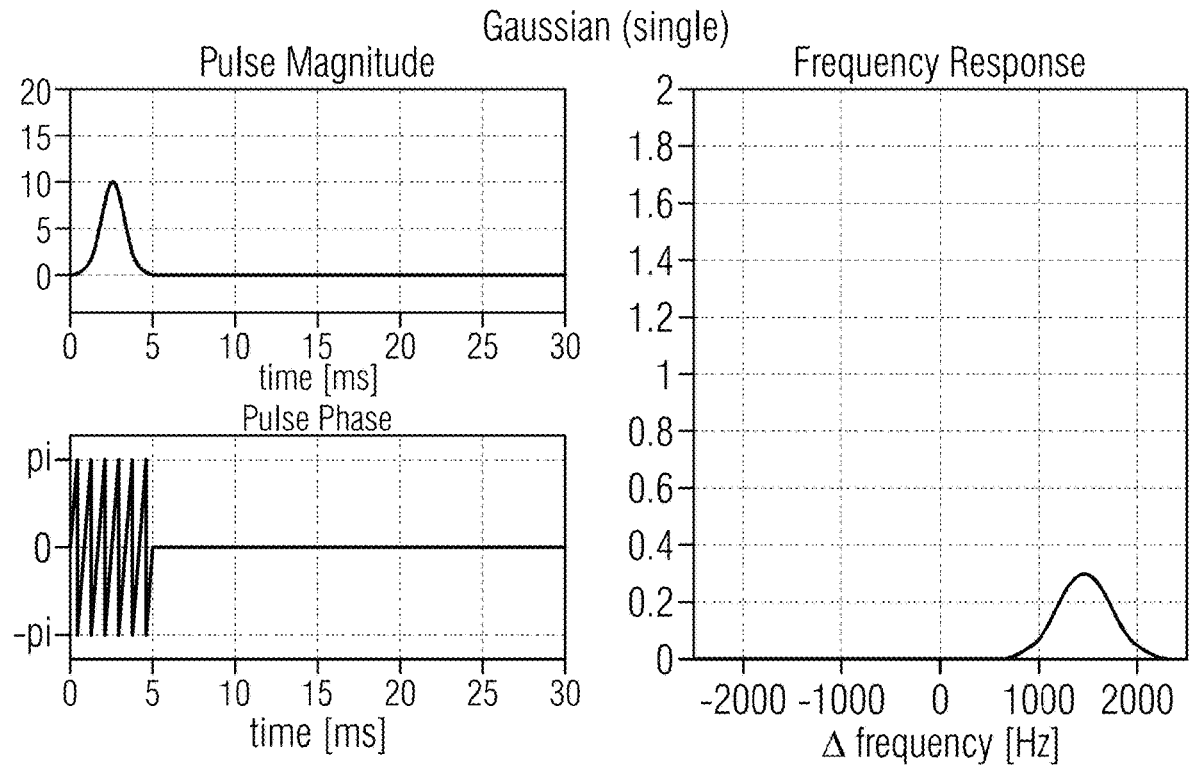
FIG. 6 shows an example for a Gaussian RF-pulse according to the state of the art.

FIG. 6 shows a single Gaussian pulse with a frequency offset Δω/2π of 1.2 kHz and a single-band Gaussian frequency characteristic. The disadvantage is a small MT-effect.

Figure 7:
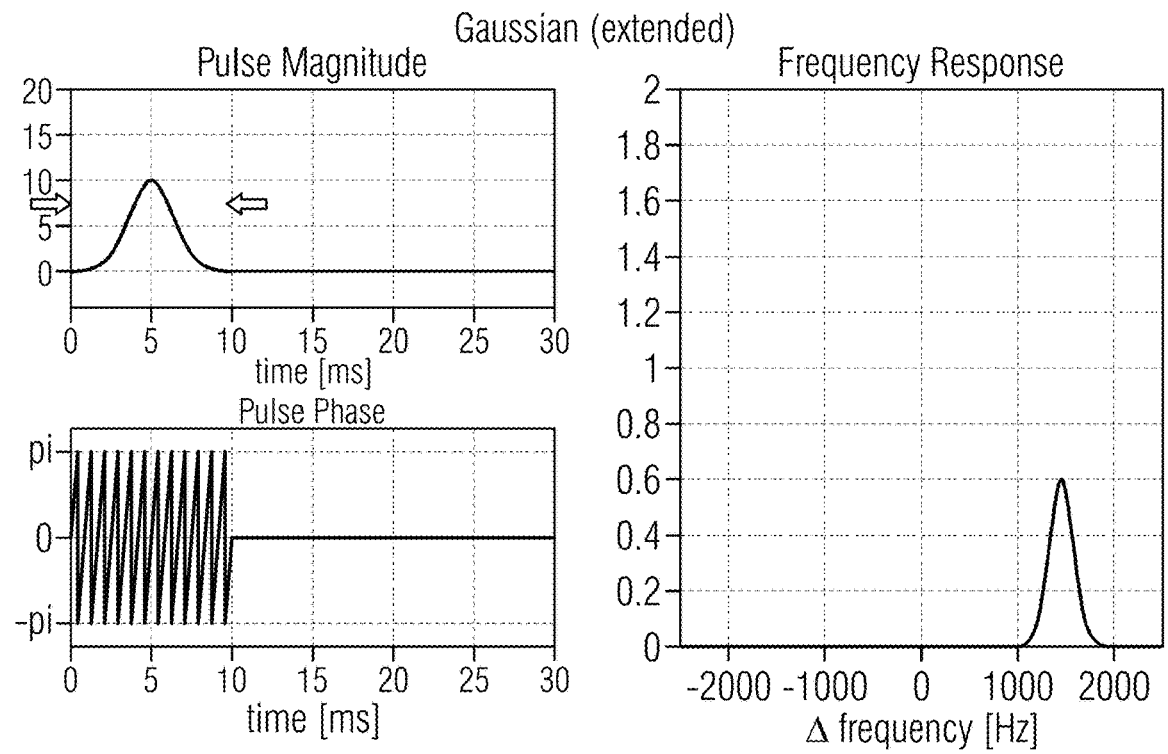
FIG. 7 shows an example for Gaussian RF-pulse according to the state of the art.

FIG. 7 shows an extended single Gaussian pulse with a frequency offset Δω/2π of 1.2 kHz and a single-band Gaussian frequency characteristic. The disadvantage is a long duration for only a moderate MT-effect.

FIG. 8 shows two adjacent Gaussian pulses (with frequency alternation) with frequency offsets Δω/2π of ±1.2 kHz and a dual-band Gaussian frequency characteristic. The disadvantage is a long duration for only a moderate MT-effect.

FIG. 9 shows a dual-band Gaussian pulse with frequency offsets Δω/2π of ±1.2 kHz and a dual-band Gaussian frequency characteristic. The disadvantage is a high peak RF-amplitude.

FIG. 10 shows a rectangular pulse with a frequency offset Δω/2π of +1.2 kHz and a single-band Sinc frequency characteristic. The disadvantage is besides a long duration a pre-saturation of on-resonance spins.

In the following, some properties of the examples of FIGS. 6 to 10 are listed, Disadvantageous values are marked with a "!".

| Figure | 6 | 7 | 8 | 9 | 10 |
|---|---|---|---|---|---|
| Duration T [ms] | 5 | 10 ! | 10 ! | 5 | 10 |
| Temporal Width Par. σ [ms] | 1 | 2 | 1 | 1 | |
| Peak RF amplitude [a.u.] | 10 | 10 | 10 | 20 ! | 10 |
| Pulse energy E [a.u.] | 125 ! | 250 | 250 | 250 | 1000 |

With a limited RF peak amplitude, rectangular RF-pulse shapes allow to apply the maximum RF-intensity within a given duration and might thus appear as be the best choice regarding the effectiveness for generating MT-contrast. However, it turns out that the frequency spectra of rectangular RF-pulses exhibit non-negligible on-resonance contributions, which lead to undesirable pre-saturation of the hydrogen nuclei to be imaged.

The principles of FIGS. 6 to 10 may get applied to other spatially non-selective excitations resp. saturations of specific frequency bands. For example, a simultaneous chemically selective saturation of fat protons (with a chemical shift of e.g. 3 ppm resulting in a frequency offset of 380 Hz at 3 T) and of silicone protons (e.g. 5.5 ppm resulting in a frequency offset of 700 Hz at 3 T) requires the application of two RF-pulses with the desired frequency offsets and bandwidths. Here the above mentioned Sinc envelope (equation 2) are applied.

FIG. 11 shows two adjacent Sinc RF-pulses with the two frequencies 380 Hz and 700 Hz and a dual-band rectangular frequency characteristic. The disadvantage is a long duration.

FIG. 12 shows a dual-band Sinc RF-pulse with the two frequencies 380 Hz and 700 Hz and a dual-band rectangular frequency characteristic. The disadvantage is a high peak RF-amplitude.

In the following, some properties of the examples of FIGS. 11 and 12 are listed, Disadvantageous values are marked with a "!".

| Figure | 11 | 12 |
|---|---|---|
| Duration T [ms] | 60 ! | 30 |
| Temporal Width Par. σ [ms] | 2, 5 | 2, 5 |
| Peak RF amplitude [a.u.] | 10 | 20 ! |

Figure 13:
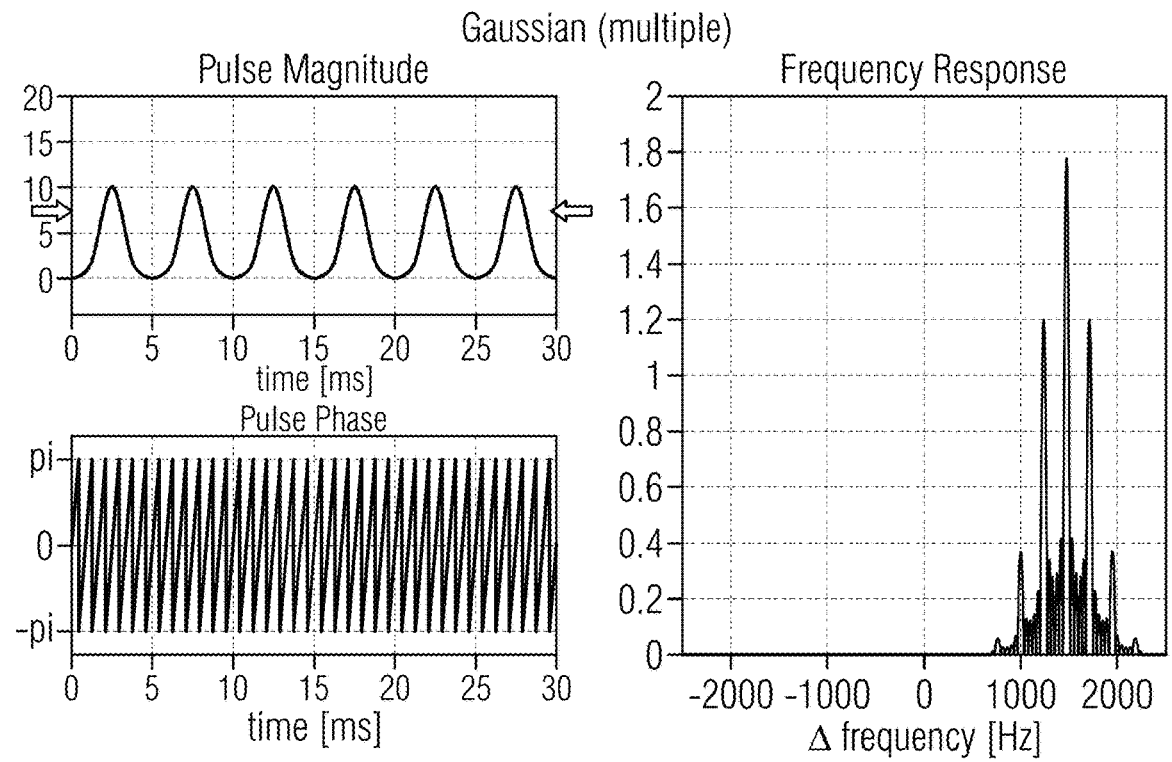
FIG. 13 shows an example for multiple Gaussian RF-pulses according to the state of the art.
Figure 14:
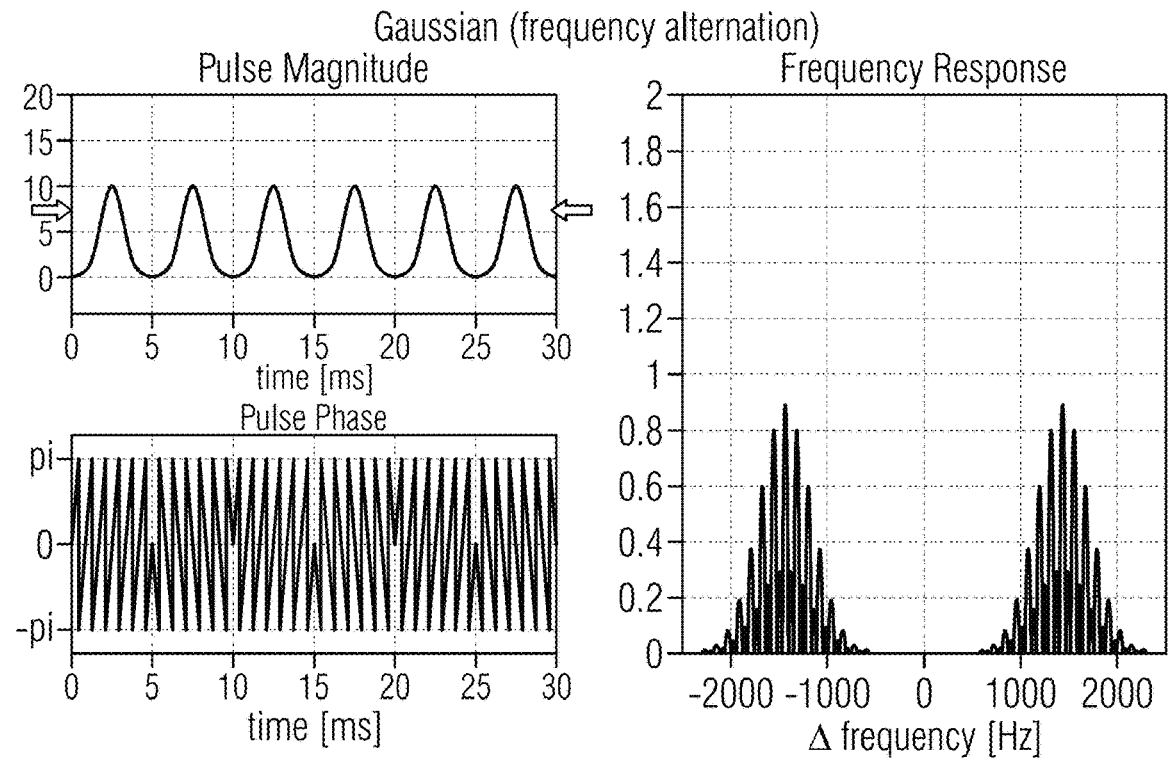
FIG. 14 shows an example for multiple Gaussian RF-pulses according to the state of the art.

If the actual shape of the frequency spectrum doesn't matter, as long as there is negligible pre-saturation of magnetization which shall get used for imaging purposes, it is possible to apply a series of preparation pulses, e.g. in order to amplify the magnetization transfer effect. FIGS. 13 and 14 show two state of the art examples.

FIG. 13 shows a series of 6 adjacent Gaussian RF-pulses with a frequency offset Δω/2π of 1.2 kHz and with a Single-band non-Gaussian frequency characteristic. The disadvantage is a long duration.

FIG. 14 shows a series of 6 adjacent Gaussian RF-pulses with a frequency offset Δω/2π of 1.2 kHz and with a Dual-band non-Gaussian frequency characteristic. The disadvantage is a long duration.

In the following, some properties of the examples of FIGS. 13 and 14 are listed, Disadvantageous values are marked with a "!".

| Figure | 13 | 14 |
|---|---|---|
| Duration T [ms] | 30 ! | 30 ! |
| Temporal Width Par. σ [ms] | 1 | 1 |
| Peak RF amplitude [a.u.] | 10 | 10 |
| Pulse energy E [a.u.] | 750 | 750 |

Figure 15:
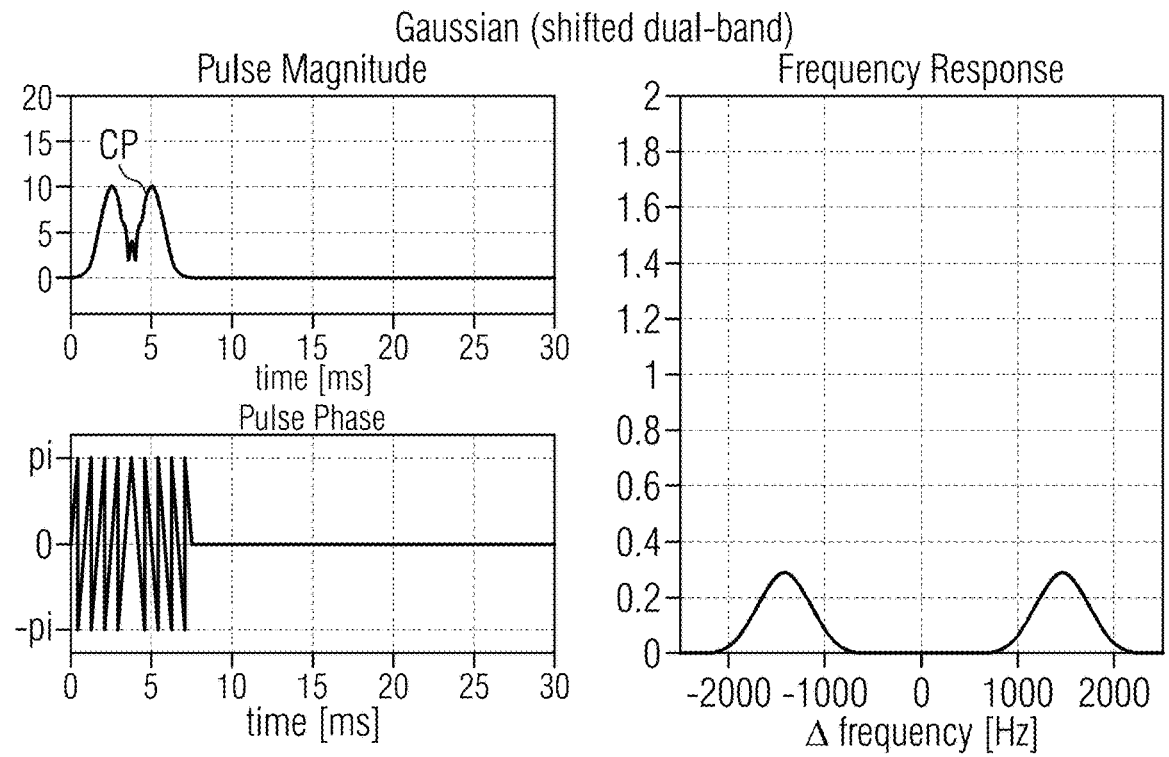
FIG. 15 shows an example for Gaussian RF-pulses according to a preferred aspect of the disclosure.
Figure 16:
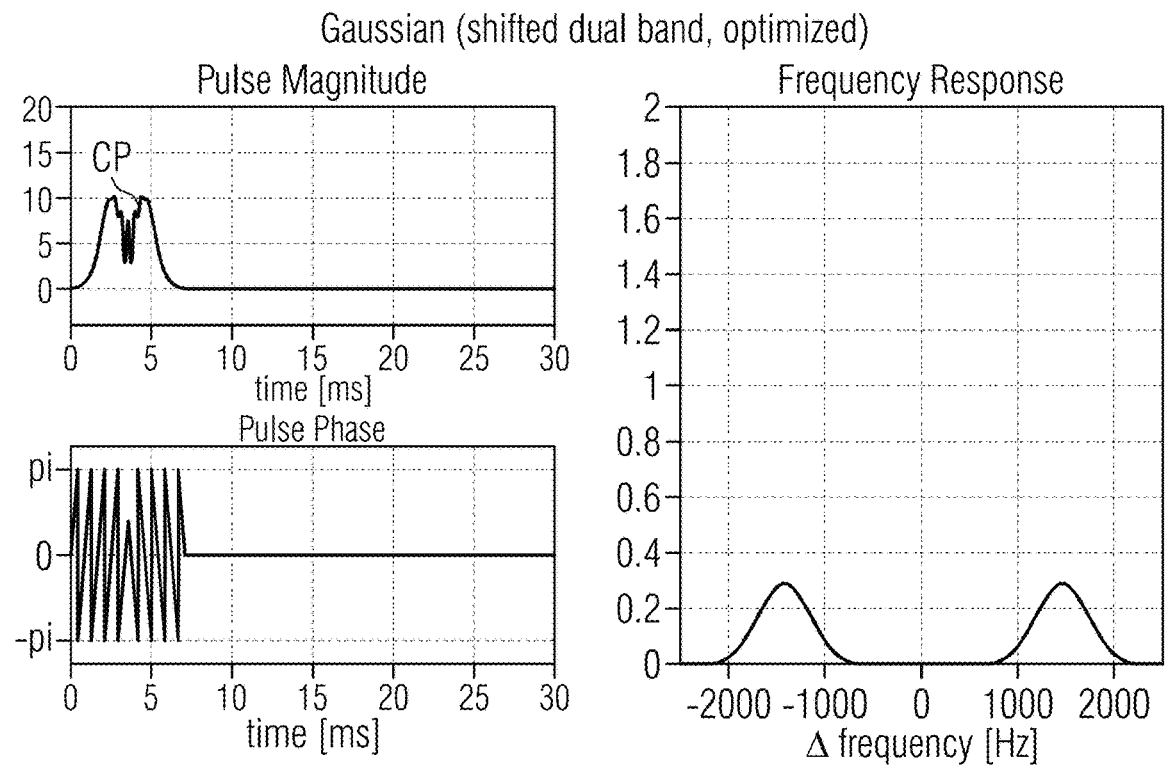
FIG. 16 shows an example for Gaussian RF-pulses according to a preferred aspect of the disclosure.

The following FIGS. 15 to 18 show a number of combined RF-pulses CP according to preferred aspects of the disclosure. FIGS. 15 and 16 correspond to cases where FIGS. 6 to 10 are referring to, FIG. 17 corresponds to Sinc pulses (see FIGS. 11 and 12) and FIG. 18 corresponds to multiple pulses (see FIGS. 13 and 14). Again, the magnitude time course of a resulting pulse (here the combined pulse CP) is shown in the upper left graph with arbitrary but compatible pulse magnitudes. On the lower left side, the phase time course is shown and on the right the frequency distribution.

FIG. 15 shows a shifted dual-band Gaussian pulse with a dual-band Gaussian frequency characteristic. In this example, the RF-pulse comprises two sub-pulses (initial RF-pulses P1, P2, see e.g. FIG. 2) with identical Gaussian shapes and identical durations of 5 ms. The frequency offsets $\Delta\omega/2\pi$ of the pulses are +1.2 kHz for one sub-pulse and −1.2 kHz for the other sub-pulse. The second sub-pulse starts 2.5 ms before the first sub-pulse ends. Due to their different frequency offsets, the overlap does not affect the frequency spectrum.

The envelope of the combined RF-pulse CP is:

$$1.\ B_1(t) = A\left(e^{-(t-t_0)^2/\sigma^2} e^{i\Delta\omega_1 t} + e^{-(t-t_0-\Delta t)^2/\sigma^2} e^{i\Delta\omega_2 t}\right). \quad (3)$$

The duration is only 7.5 ms and the peak RF amplitude 10 a.u. with a pulse energy of 250 a.u. Thus, with the selected pulse shift, the peak amplitude of the combined RF-pulse does not exceed the single-pulse maximum.

Compared with the state of the art, the pulse energy corresponds with the pulse energies of FIGS. 7 to 9 (FIG. 6 provides not enough energy) with the advantage that the pulse duration is lower than 10 ms while the peak RF amplitude is only 10 a.u.

Thus, the advantages are a stronger MT-effect as compared to FIG. 6, the same MT-effect in a shorter duration as compared to FIGS. 7 and 8 and the same MT-effect with lower RF peak-amplitude as compared to FIG. 9, wherein no pre-saturation occurs compared to FIG. 10.

FIG. 16 shows a shifted dual-band Gaussian pulse similar to FIG. 15 with the difference that the pulse shift has been set to the minimum value for which the peak amplitude of the combined RF-pulse CP does not exceed the single-pulse maximum, e.g. by an algorithm as shown in FIG. 3. The duration is only 7 ms and the peak RF amplitude 10 a.u. with a pulse energy of 250 a.u. It has the same advantages as the combined RF-pulse CF of FIG. 15 over the prior art, but with a shorter duration.

Looking at the integer ratios of energy/duration in arbitrary units of the examples, wherein any ratio under 30 and any pre saturation is not desired (FIG. 10 omitted), one get:

| Figure | 6 | 7 | 8 | 9 | 15 | 16 |
|---|---|---|---|---|---|---|
| energy E | 125 | 250 | 250 | 250 | 250 | 250 |
| Dur. T [ms] | 5 | 10 | 10 | 5 | 7.5 | 7 |
| E/T | 25 | 25 | 25 | 50 | 34 | 36 |

Thus, compared to standard preparation schemes, the disclosed subject matter can generate similar MT-effects in a shorter duration while using moderate RF peak amplitudes.

Figure 17:
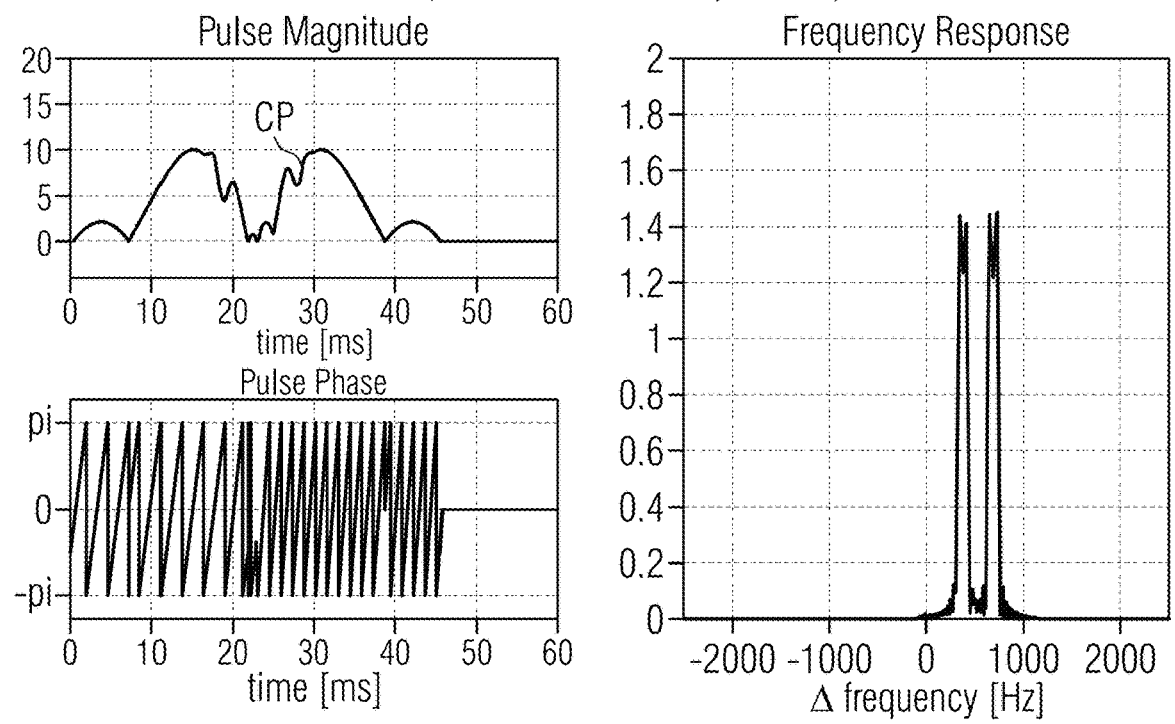
FIG. 17 shows an example for optimized Sinc RF-pulses according to a preferred aspect of the disclosure.

FIG. 17 shows an optimized shifted dual-band Sinc RF-pulse with the two frequency offsets 380 Hz and 700 Hz and a dual-band rectangular frequency characteristic. In this example, the RF-pulse comprises two sub-pulses (initial RF-pulses P1, P2, see e.g. FIG. 2) with identical shapes (Sinc) and identical durations of 30 ms. The second sub-pulse starts 14 ms before the first sub-pulse ends. Due to their different frequency offsets, the overlap does not affect the frequency spectrum. With the selected pulse shift, the peak amplitude of the combined RF-pulse does not exceed the single-pulse maximum.

The envelope of the combined RF-pulse CP is:

$$B_1(t) = A\left(\sin\left(\frac{t-t_0}{\sigma}\right)\frac{\sigma}{t-t_0} e^{i\Delta\omega_1 t} + A\ \sin\left(\frac{t-t_0-\Delta t}{\sigma}\right)\frac{\sigma}{t-t_0-\Delta t} e^{i\Delta\omega_2 t}\right). \quad (4)$$

The duration is only 46 ms and the peak RF amplitude 10 a.u. Thus, with the selected pulse shift, the peak amplitude of the combined RF-pulse does not exceed the single-pulse maximum.

Compared with the state of the art, the pulse duration is much lower than the 60 ms of the pulse shown in FIG. 11 while the peak RF amplitude is lower than of the pulse shown in FIG. 12 (20 a.u.).

Thus, the advantages are that the same saturation effect can be achieved in a shorter duration compared to FIG. 11 and the same saturation effect can be achieved with lower RF peak-power compared to FIG. 12.

Figure 18:
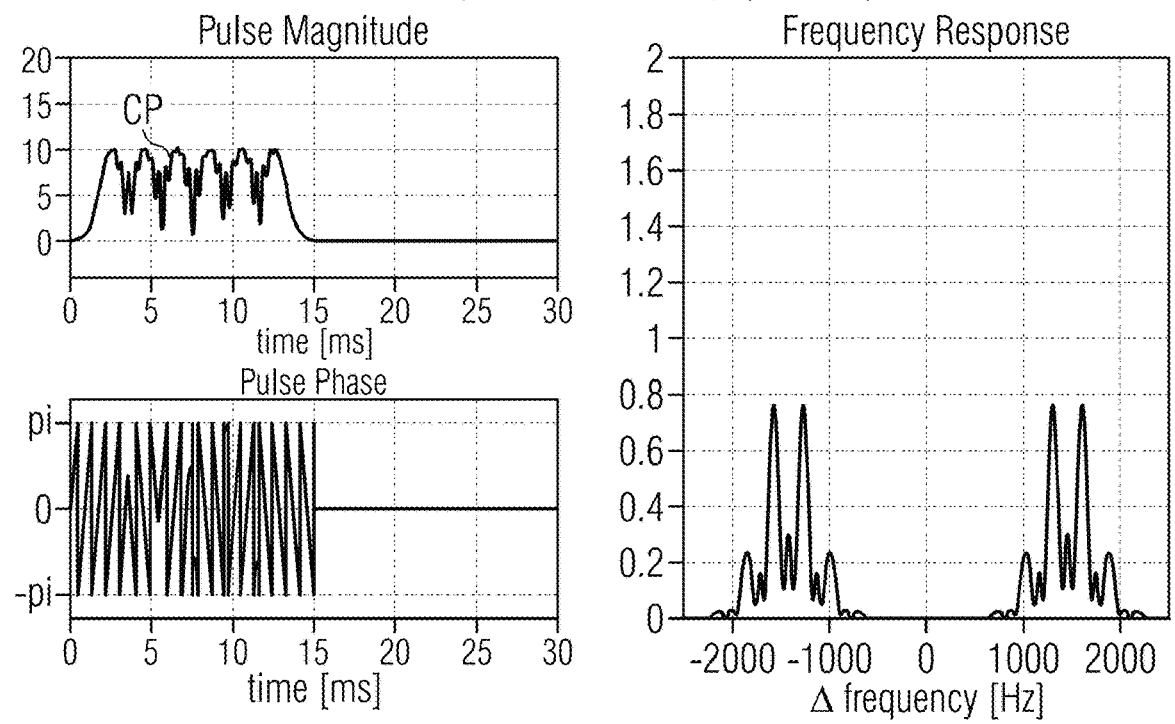
FIG. 18 shows an example for multiple Gaussian RF-pulses according to a preferred aspect of the disclosure.

FIG. 18 shows an RF-pulse with a dual-band non-Gaussian frequency characteristic. In this example, the RF-pulses comprises 6 sub-pulses (initial RF-pulses P1, P2, see e.g. FIG. 2) with identical Gaussian shapes and identical durations of 5 ms. The frequency offsets $\Delta\omega/2\pi$ of the pulses are alternating between +1.2 kHz and −1.2 kHz for adjacent sub-pulses. Each succeeding sub-pulse starts 2000 µs before the preceding sub-pulse ends: this ensures that sub-pulses with identical frequency offset do not overlap, which preserves desirable frequency spectrum.

The duration is only 15 ms and the peak RF amplitude 10 a.u. with a pulse energy of 750 a.u. Thus, with the selected pulse shift, the peak amplitude of the combined RF-pulse does not exceed the single-pulse maximum.

Compared with the state of the art, the pulse energy corresponds with the pulse energies of FIGS. 13 and 14 with the advantage that the pulse duration is much lower than 30 ms. Thus, the advantages are that the same saturation effect can be achieved in a shorter duration compared to FIGS. 13 and 14.

Although the disclosed subject matter is in the form of preferred aspects and variations thereon, it will be understood that numerous additional modifications and variations could be made thereto without departing from the scope of the disclosed subject matter. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The invention claimed is:

1. A method for controlling a magnetic resonance imaging system, comprising:
    selecting a plurality of spatially non-selective initial radio frequency (RF)-pulses, each having a predefined pulse shape and a predefined frequency;
    determining a combined RF-pulse from the plurality of spatially non-selective initial RF-pulses by determining a time-offset comprising a relative application time-shift and a phase-shift between the plurality of spatially non-selective initial RF-pulses,
    wherein the time-offset is determined in accordance with the predefined pulse shape and the predefined frequency of the plurality of spatially non-selective initial RF-pulses such that the plurality of spatially non-selective initial RF-pulses overlap; and
    including the combined RF pulse in a pulse sequence applied in the magnetic resonance imaging system.

2. The method according to claim 1, wherein the plurality of spatially non-selective initial RF-pulses are designed for a spatially non-selective excitation of proton spins, for pulse sequences designed for magnetization transfer, a chemically selective saturation, or a chemical exchange saturation transfer.

3. The method according to claim 1, wherein two of the plurality of spatially non-selective initial RF-pulses have a different frequency with separate, non-overlapping frequency bands, and the difference between the frequencies is more than 50 Hz.

4. The method according to claim 1, wherein the time-offset is determined such that an absolute value of a maximum RF-intensity of the combined RF-pulse does not exceed a predefined maximum RF-intensity that is lower than a maximum RF-intensity of the magnetic resonance imaging system or an absolute value of a maximum RF-intensity of the plurality of spatially non-selective initial RF-pulses.

5. The method according to claim 1, wherein the predefined pulse shape B1(t) of a number of the plurality of spatially non-selective initial RF-pulses with an amplitude A follows the formula:

$$B_1(t) = Ae^{-(t-t_0)^2/\sigma^2}e^{i\Delta\Delta\omega} \text{ or } B_1(t) = A\sin\left(\frac{t-t_0}{\sigma}\right)\frac{\sigma}{t-t_0}e^{i\Delta\omega t}.$$

and wherein:
t represents time,
$t_0$ to represents a center of the plurality of spatially non-selective initial RF-pulses,
σ represents a temporal width parameter,
Δω represents a frequency offset, and
i represents an imaginary number $\sqrt{-1}$.

6. The method according to claim 1, wherein the predefined pulse shape and/or a duration of a number of the plurality of spatially non-selective initial RF-pulses is identical, and a number of the plurality of spatially non-selective initial RF-pulses have different frequency offsets.

7. The method according to claim 1, wherein two of the plurality of spatially non-selective initial RF-pulses are arranged such that there is a temporal overlap therebetween having a non-empty set of time points, and
wherein an RF-contribution of the two of the plurality of spatially non-selective initial RF-pulses is non-zero.

8. The method according to claim 1, wherein the time-offset is determined such that a minimal temporal shift between two of the plurality of spatially non-selective initial RF-pulses is determined, with the steps:
a) providing predefined pulse shapes of the plurality of spatially non-selective initial RF-pulses;
b) providing a predefined minimal test-offset comprising a time-shift and a phase-shift with the value zero;
c) providing a predefined maximum RF-intensity of the combined RF-pulse;
d) calculating a summed RF-pulse of the plurality of spatially non-selective initial RF-pulses, where at least one of the plurality of spatially non-selective initial RF-pulses is temporally shifted with the test-offset; and
e) comparing an absolute value of the--a maximum RF-intensity of the summed RF-pulse with the predefined maximum RF-intensity of the combined RF-pulse,
when the absolute value of the maximum RF-intensity of the summed RF-pulse exceeds the predefined maximum RF-intensity of the combined RF-pulse, increasing the test-offset between the two of the plurality of spatially non-selective initial RF-pulses with a predefined temporal value and repeat steps d) to e), and
when the absolute value of the maximum RF-intensity of the summed RF-pulse does not exceed the predefined maximum RF-intensity of the combined RF-pulse, taking the summed RF-pulse as the combined RF-pulse,
wherein the steps are performed until the time-shift of the test-offset exceeds a length of the plurality of spatially non-selective initial RF-pulses such that the plurality of spatially non-selective initial RF-pulses no longer overlap.

9. The method according to claim 8, wherein in the course of increasing the test-offset, the time-shift is increased by a predefined positive or negative shift, or a phase-shift is increased by a positive or negative shift until the phase-shift exceeds a value of 2π, and
wherein the phase-shift is increased in an inner loop and the time-shift is increased in an outer loop.

10. The method according to claim 8, wherein the time-offset is determined such that an absolute value of the maximum RF-intensity of the combined RF-pulse does not exceed a predefined maximum RF-intensity.

11. The method according to claim 1, wherein the time-offset is determined by iteratively adjusting the relative application time-shift and the phase-shift based upon a predetermined RE pulse amplitude constraint, a predetermined time-shift constraint, and a predetermined phase-shift constraint such that the plurality of spatially non-selective initial RF-pulses overlap in the time domain but not in the frequency domain.

12. A system for controlling a magnetic resonance imaging system, comprising:
a selector configured to select a plurality of spatially non-selective initial radio frequency (RF)-pulses, each having a predefined pulse shape and a predefined frequency;
a determiner configured to determine a combined RF-pulse from the plurality of spatially non-selective initial RF-pulses by determining a time-offset comprising a relative application time-shift and a phase-shift between the plurality of spatially non-selective initial RF-pulses,
wherein the time-offset is determined in accordance with the predefined pulse shape and the predefined frequency of the plurality of spatially non-selective initial RF-pulses such that the plurality of spatially non-selective initial RF-pulses overlap; and
a sequence controller configured to include the combined RF pulse in a pulse sequence applied by a radio-frequency transmitter of the magnetic resonance imaging system.

13. The magnetic resonance imaging system of claim 12, further comprising:
a controller configured to control the magnetic resonance imaging system.

14. A non-transitory computer-readable medium configured to store computer-readable instructions that, when read and executed by a computer of a magnetic resonance imaging system, cause the magnetic resonance imaging system to:
select a plurality of spatially non-selective initial RF-pulses, each having a predefined pulse shape and a predefined frequency;

determine a combined RF-pulse from the plurality of spatially non-selective initial RF- pulses by determining a time-offset comprising a relative application time-shift and a phase-shift between the plurality of spatially non-selective initial RF-pulses,
wherein the time-offset is determined in accordance with the predefined pulse shape and the predefined frequency of the plurality of spatially non-selective initial RF-pulses such that the plurality of spatially non-selective initial RF-pulses overlap; and
include the combined RF pulse in a pulse sequence applied by the magnetic resonance imaging system.

\* \* \* \* \*